United States Patent
Price

(10) Patent No.: US 10,577,289 B2
(45) Date of Patent: Mar. 3, 2020

(54) VERMICULTURE BIOREACTOR SYSTEM AND METHOD OF USE

(71) Applicant: Earnest Earth Agriculture, Inc., Lynn Center, IL (US)

(72) Inventor: Gabriel Price, Lynn Center, IL (US)

(73) Assignee: EARNEST EARTH AGRICULTURE, INC., Lynn Center, IL (US)

( * ) Notice: Subject to any disclaimer, the term of this patent is extended or adjusted under 35 U.S.C. 154(b) by 0 days.

(21) Appl. No.: 16/217,626

(22) Filed: Dec. 12, 2018

(65) Prior Publication Data

US 2019/0218153 A1 Jul. 18, 2019

Related U.S. Application Data

(60) Provisional application No. 62/617,221, filed on Jan. 13, 2018.

(51) Int. Cl.
| | | |
|---|---|---|
| *C05F 17/02* | (2006.01) | |
| *C05F 17/00* | (2006.01) | |
| *A01K 67/033* | (2006.01) | |

(52) U.S. Cl.
CPC ...... *C05F 17/0205* (2013.01); *C05F 17/0009* (2013.01); *A01K 67/0332* (2013.01)

(58) Field of Classification Search
CPC .. C05F 17/0009; C05F 17/02; C05F 17/0205; C05F 17/00; C05F 9/04; C05F 17/0258
USPC ................... 71/9, 14, 23; 210/602
See application file for complete search history.

(56) References Cited

U.S. PATENT DOCUMENTS

| | | | | |
|---|---|---|---|---|
| 6,699,708 B1* | 3/2004 | Muller | ...................... | B09B 3/00 435/262 |
| 2003/0059931 A1* | 3/2003 | Gitt | ...................... | C05F 17/0205 435/290.1 |
| 2008/0251021 A1* | 10/2008 | Herlihy | .............. | A01K 67/0332 119/6.7 |
| 2012/0285209 A1* | 11/2012 | Bassile | ............... | C05F 17/0223 71/8 |
| 2016/0193951 A1* | 7/2016 | Maertens | .................. | B60P 1/56 298/27 |
| 2016/0207845 A1* | 7/2016 | Delgado | ............. | C05F 17/0247 |

FOREIGN PATENT DOCUMENTS

WO  WO-0246127 A2 *  6/2002  ................ C05F 9/04

OTHER PUBLICATIONS

Kim KR 2002-0015607 English Abstract (Year: 2002).*

* cited by examiner

*Primary Examiner* — Claire A Norris
(74) *Attorney, Agent, or Firm* — Wilson Sonsini Goodrich & Rosati

(57) ABSTRACT

A portable, climate-controlled, continuous flow-through, computer-operated vermiculture bioreactor and method for the treatment of organic solid wastes utilizing accelerated microbiological decomposition including composting and vermicomposting to convert materials into environmentally compatible products, including stable biofertilizer. The portable bioreactor design converts carbon-based organic waste into biofertilizer using thermophilic composting, vermicastings and vermicomposting that can be used directly for plant and farming applications.

18 Claims, 11 Drawing Sheets

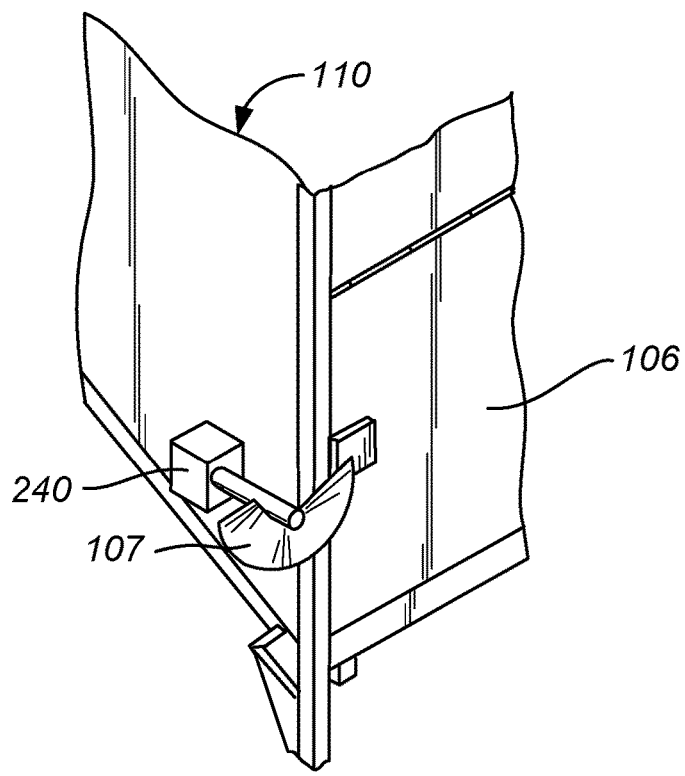
*FIG. 6A*
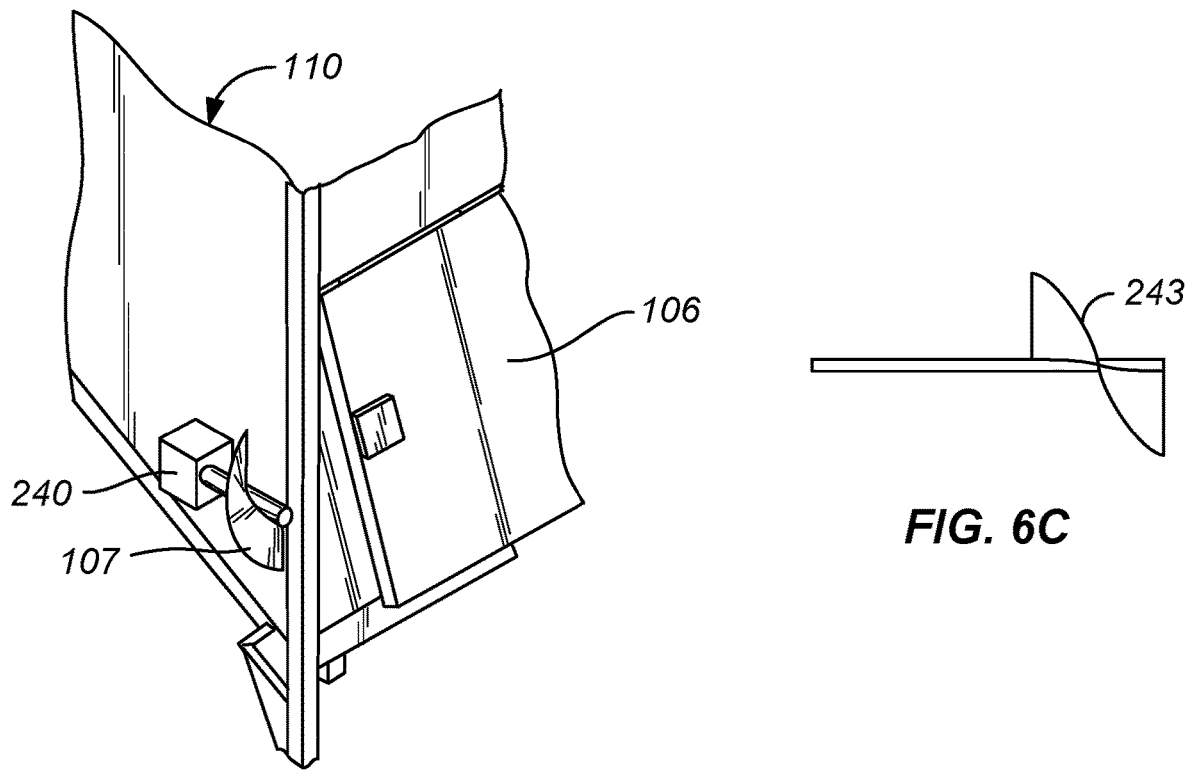
*FIG. 6B*
*FIG. 6C*

VERMICULTURE BIOREACTOR SYSTEM AND METHOD OF USE

CROSS-REFERENCE

This application claims the benefit of U.S. Provisional Application No. 62/617,221, filed Jan. 13, 2018, which application is incorporated herein by reference.

BACKGROUND OF THE INVENTION

The present invention relates to an apparatus and method for the treatment of organic solid wastes and more particularly, to the treatment of organic wastes utilizing accelerated microbiological decomposition including composting and vermicomposting to convert materials into environmentally compatible products, including stable biofertilizer. More particularly, the present invention relates to a portable, computer-operated bioreactor design that converts organic waste into biofertilizer using thermophilic composting, vermicastings and vermicomposting.

SUMMARY OF THE INVENTION

Additional aspects and advantages of the present disclosure will become readily apparent to those skilled in this art from the following detailed description, wherein only exemplary embodiments of the present disclosure are shown and described, simply by way of illustration of the several modes or best mode contemplated for carrying out the present disclosure. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Provided herein is a portable, climate-controlled, continuous flow-through, computer-operated vermiculture bioreactor and method for the treatment of organic solid wastes utilizing accelerated microbiological decomposition including thermophilic composting and vermicomposting to convert materials into environmentally compatible products, including stable biofertilizer. The portable bioreactor design converts carbon-based organic waste into biofertilizer using thermophilic composting, vermicastings and vermicomposting that can be used directly for plant and farming applications.

Provided herein is a vermiculture bioreactor system for converting raw organic waste matter into a stable biofertilizer utilizing thermophilic composting and vermicomposting, the bioreactor comprising: a decomposing chamber for containing the organic waste matter during thermophilic composting and lignin degradation, the decomposing chamber configured to direct the thermophilically composted organic waste matter to a vermicomposting chamber; and a plurality of sensors for monitoring an environmental condition of at least one of the bioreactor chambers and the organic waste matter during the thermophilic decomposition and vermicomposting; wherein the vermicomposting chamber is configured to receive the thermophilically composted organic waste matter from the decomposing chamber and is further configured to contain the thermophilically composted organic waste matter during vermicomposting thereof.

In any embodiment, the bioreactor system further comprises a temperature control system.

In any embodiment, the bioreactor system further comprises a forced-air system coupled to the decomposing chamber for directing air into the decomposing chamber and maintaining the contained organic waste matter within a thermophilic temperature range.

In any embodiment, the bioreactor system further comprises a computer-implemented system comprising: a digital processing device comprising: at least one processor; an operating system configured to perform executable instructions; a memory; and at least one computer program including instructions executable by the digital processing device configured to interface with and control the bioreactor, bioreactor sub-components and the sensors, and communicate with remote monitoring facilities and/or take advantage of cloud computing and storage with a receiver/transmitter device.

In any embodiment, the bioreactor system further comprises a base in the decomposing chamber having a downward slope configured to promote gravity transfer of the thermophilically composted organic waste matter from the decomposing chamber to the vermicomposting chamber.

In any embodiment of the bioreactor system, a movement of the organic waste matter through the bioreactor is accomplished via gravity.

In any embodiment, the bioreactor system further comprises a release door in the decomposing chamber configured to accommodate the release and transfer of the thermophilically composted organic matter waste from the decomposing chamber to the vermicomposting chamber.

In any embodiment of the decomposing chamber, the slope of the base is about 30°. In some embodiment, the downward slope of the base is equal to or greater than about 30°. In some embodiments, the downward slope of the base is equal to or less than about 30°.

However, depending on the lubricity of the sloped surface, the slope of the base can have a range anywhere between about 10.0° and about 60.0°.

In any embodiment, the bioreactor system further comprises at least one auger-type mechanism.

In any embodiment, the bioreactor system further comprises a high-torque stepper motor, motor controller and relay to drive the at least one auger-type mechanism.

In any embodiment of the bioreactor system, a movement of the organic waste matter through the bioreactor is accomplished via the at least one auger-type mechanism. This at least one auger-type mechanism can be any form of known auger-type mechanism utilized as a conveyance means to move (typically granular and slurry) materials.

In any embodiment, the bioreactor system further comprises a locking mechanism.

In some embodiments, the locking mechanism is capable of opening and then closing the release door to assure closure against soft and/or friable debris that may obstruct the door after allowing the organic waste matter to pass between the decomposing chamber and vermicomposting chamber.

In any embodiments of the bioreactor system, the locking mechanism is an auger-type locking mechanism.

In any embodiments of the bioreactor system, the bioreactor further comprises a high-torque stepper motor, motor controller and relay to drive the auger-type locking mechanism.

In any embodiments of the bioreactor system, the vermicomposting chamber is below the decomposing chamber and is configured to hold a plurality of annelids for consuming the thermophilically composted organic waste matter received from the decomposing chamber.

In any embodiments of the bioreactor system, the vermicomposting chamber further comprises a porous bottom surface.

In any embodiments of the bioreactor system, the porous bottom surface comprises at least one of: a screen; a wire mesh; a grid: straining surface and a sieve.

In any embodiments of the bioreactor system, the porous bottom surface has a plurality of sieve or mesh openings having a size of about 1.0 inch (25.4 mm).

In any embodiment of the bioreactor, the porous bottom surface has a plurality of sieve or mesh openings having a size between about 4.0 inches (101.6 mm) or smaller and about 0.158 inch (4.0 mm) or greater.

In any embodiments of the bioreactor system, the vermicomposting chamber further comprises a cutting bar configured to periodically traverse the length of the chamber, near the bottom, to encourage the processed biofertilizer to fall through the porous bottom surface.

Optionally, in any of the embodiments, the bioreactor system further comprises a removable receptacle for capturing the stable biofertilizer dropping through the porous bottom surface.

In any embodiment of the bioreactor system, the bioreactor is portable.

In any embodiment, the bioreactor system is configured for continuous flow-through operation.

In any embodiments of the bioreactor system, each chamber of the bioreactor has a minimum capacity of 1.0 m$^3$.

In any embodiment, the bioreactor system further comprises a solar panel and DC battery power system.

In any embodiment, the bioreactor system further comprises a power bank to store energy and perform step-down voltage requirements.

In any embodiment of the bioreactor system, the power system comprises two or more solar panels.

In any embodiment of the bioreactor system, the DC battery comprises a deep-cycle battery.

In any embodiment of the bioreactor system, the system further comprises at least one high-torque stepper motor, at least one motor controller and at least one relay to drive any one of a plurality of pumps and valving.

In any embodiment, the bioreactor system further comprises injectors in the decomposing chamber connected to a pump and valves configured to add water to the decomposing organic waste matter to ensure that adequate moisture is maintained throughout the composting process.

In any embodiment, the bioreactor system further comprises a plurality of inoculating pumps and valves configured to inoculate both the decomposing chamber and the vermicomposting chamber with a plurality of microbial inoculum, hormones and nutrients.

In any embodiment of the bioreactor system, the inoculating pumps and valves are connected to the injectors.

In any embodiment of the bioreactor system, the microbial inoculua of the decomposing chamber comprise lignin-degrading fungi and bacteria.

In any embodiment of the bioreactor system, the fungi comprise at least one of: arbuscular mycorrhiza fungi (AMF); *Trametes versicolor; Phanerochaete chrysosporium; Basidiomycetes; Ascomycetes* and *Deuteromycetes*.

In any embodiment of the bioreactor system, the bacteria comprise at least one of: *Pseudomonas; Flavobacterium*; filimentous bacteria or Actinomycetes and *Thermus* bacteria.

In any embodiment of the bioreactor system, the microbial inoculua of the vermicomposting chamber comprise microbes beneficial to plant use and can perform at least one of the following functions: promote nutrient acquisition; promote plant growth; promote plant health; promote disease prevention; promote drought resistance; promote insect resistance and kill insects.

In any embodiment of the bioreactor system, the beneficial microbes comprise at least one of: rhizobia; *Azotobacter; Bacillus subtilis; Acetobacter*; Phosphorus solubilizing microorganisms; blue-green cyanobacteria and arbuscular mycorrhiza fungi (AMF).

In any embodiment of the bioreactor system, the nutrients comprise at least one of: calcium carbonate; magnesium; crushed limestone; carbon; urea; potassium; phosphorous and nitrogen.

In any embodiment of the bioreactor system, the hormones of the vermicomposting chamber comprise at least one of: Indole-3-acetic acid; gibberellic acid; auxins; cytokinins; gibberellins, abscisic acid and ethylene.

In any embodiment of the bioreactor system, the plurality of sensors comprise at least one of: a temperature sensor; a relative humidity sensor; a moisture sensor; a chemical sensor; an $O_2$ sensor; a $N_2$ sensor; a $CO_2$ sensor and a pH sensor; each configured to interface with a computer-implemented system.

In any embodiment of the bioreactor system, the decomposing chamber is configured to reach a thermophilic temperature greater than at least about 50° C. (122° F.) but less than about 76° C. (169° F.), for a minimum period of time necessary to substantially render any pathogens harmless to humans before further allowing the organic waste matter temperature to drop to an ambient temperature at a natural thermophilic rate.

In any embodiment of the bioreactor system, the organic waste matter is configured to reach a thermophilic temperature of greater than at least about 55° C. (131° F.).

In any embodiment of the bioreactor system, an ambient temperature of the organic waste matter in the vermiculture chamber is between about 10° C. (50° F.) and about 29° C. (84° F.).

In any embodiment of the bioreactor system, the ambient temperature of the organic waste matter in the vermiculture chamber is controlled by the temperature control system.

In any embodiment of the bioreactor system, the organic waste matter temperature is prevented from exceeding a maximum thermophilic temperature with the temperature control system.

In any embodiment of the bioreactor system, the temperature control system comprises at least one of: a vented ducting arrangement, valving and a pump for forced air infusion; a closed ducting arrangement, valving and a pump for water cooling; a closed ducting arrangement, valving and a pump for refrigerant-type cooling; an automated turning system to disrupt the organic waste matter; an infrared system; a closed ducting arrangement, valving and pump for water heating; an electric coiled system for heating; and a gas burner system for heating.

In any embodiment of the bioreactor system, the computer-implemented system further comprises non-transitory computer-readable storage media encoded with a computer program including instructions executable by the processor to create an application comprising: at least one software module comprising instructions configured to perform at least one of: interface with and control the function of the bioreactor, the bioreactor sub-components, and the sensors, and communicate with remote monitoring facilities throughout the composting process; and collect, store and report environmental data regarding each chamber of the bioreactor or sub-components thereof.

In any embodiment of the bioreactor system, the computer-implemented system further comprises the ability to take advantage of cloud computing and storage of data.

Provided herein is a method of converting organic waste matter into a stable biofertilizer utilizing thermophilic composting and vermicomposting comprising: a) providing a portable, climate-controlled, continuous flow-through, computer-operated vermiculture bioreactor comprising: a gravity-fed, thermophilic decomposing chamber; and an interconnected vermicomposting chamber; wherein the thermophilic decomposing chamber comprises a gravity-feeding inferior surface positioned at a downward slope equal to about 30° relative to a side release door; b) providing an organic waste with biologic origins, primarily composing carbon and nitrogen; c) depositing said organic waste in the gravity-fed, thermophilic decomposing chamber; d) controlling the temperature of said organic waste to heat to a thermophilic temperature between at least about 50° C. (122° F.)-55° C. (131° F.), but less than about 76° C. (169° F.) for a time sufficient to substantially render any pathogens harmless to humans; e) controlling the temperature of said heated organic waste matter to cool to an ambient temperature at a natural thermophilic rate; f) inoculating said organic waste matter with lignin-degrading fungi and bacteria; g) controlling a temperature, a relative humidity, a moisture and a pH of said organic waste; h) infusing adequate air and water into the organic waste matter to ensure aerobic composting; i) promoting thermophilic composting for a time sufficient to break down the lignin in the organic waste with thermophilic bacteria to an acceptable state; j) transferring the thermophilically composted organic waste to the interconnected vermicomposting chamber; k) controlling the temperature of the interconnected vermicomposting chamber between at least about 10° C. (50° F.) and about 2.9° C. (84° F.): l) providing adequate quantities of annelids in the interconnected vermicomposting chamber to assure a predictable rate of vermicomposting; m) inoculating said composted organic waste in the vermicomposting chamber with a plurality of microbial inoculum, hormones and nutrients; n) removing a portion of the vermicastings and granular biofertilizer generated by the vermicomposting in an automated fashion from the bottom of the vermicomposting chamber, at a scheduled rate coinciding with the predictable rate of vermicomposting; and o) repeating steps b)-o).

In any embodiment, the method further comprises, providing perforated aeration ducting arrangement, valving and an air pump to provide forced aeration to ensure aerobic composting.

In any embodiment, the method further comprises, providing a computer-implemented system comprising: a digital processing device comprising: at least one processor; an operating system configured to perform executable instructions; a memory and at least one computer program including instructions executable by the digital processing device configured to interface with and control the bioreactor, bioreactor sub-components and the sensors, and communicate with remote monitoring facilities and/or take advantage of cloud computing and storage with a receiver/transmitter device.

In any embodiment, the method further comprises providing the computer-implemented system with the ability to take advantage of cloud computing and storage of data.

In any embodiment, the method further comprises, providing at least one of: a temperature sensor; a relative humidity sensor; a moisture sensor; a chemical sensor; an $O_2$ sensor; a $N_2$ sensor; a $CO_2$ sensor and a pH sensor; each configured to interface with the computer-implemented system.

In any embodiment, the method further comprises, providing a locking mechanism.

In some embodiments of the method, the locking mechanism is an auger-type locking mechanism capable of opening and then closing the side release door to assure closure against soft and/or friable debris that may obstruct the door after allowing the organic waste matter to pass between the decomposing chamber and vermicomposting chamber.

In any embodiment, the method further comprises, providing at least one high-torque stepper motor, at least one motor controller and at least one relay to drive any one of a plurality of pumps and valving.

In some embodiments of the method, the high-torque stepper motor, motor controller and relay are interfaced with the auger-type locking mechanism and the computer-implemented system.

In any embodiment, the bioreactor system further comprises at least one auger-type mechanism.

In any embodiment of the method, the bioreactor system further comprises a high-torque stepper motor, motor controller and relay to drive the at least one auger-type mechanism.

In any embodiment of the method, a movement of the organic waste matter through the bioreactor is accomplished via the at least one auger-type mechanism. This at least one auger-type mechanism can be any form of known auger-type mechanism utilized as a conveyance means to move (typically granular and slurry) materials.

In some embodiments of the method, the high-torque stepper motor, motor controller and relay are interfaced with the auger-type mechanism and the computer-implemented system.

In any embodiment of the method, the plurality of microbial inoculum, nutrients and hormones injected into the vermicomposting chamber comprise at least one of: the beneficial microbes comprising at least one of: rhizobia; and blue-green cyanobacteria; and the beneficial fungi comprise at least one of: arbuscular mycorrhiza fungi (AMF); *Trametes versicolor; Phanerochaete chrysosporium; Basidiomycetes; Ascomycetes* and *Deuteromycetes*; and the nutrients comprising at least one of: calcium carbonate; magnesium; crushed limestone; carbon; urea; potassium; phosphorous and nitrogen; and the hormones comprising at least one of: Indole-3-acetic acid; gibberellic acid; auxins; cytokinins; gibberellins; abscisic acid and ethylene, or any combination of the optional plurality of microbial inoculum, nutrients and hormones recited herein.

In any embodiment of the method, the computer-implemented system of the bioreactor system further comprises the ability to take advantage of cloud computing and storage of data.

Provided herein is a portable, climate-controlled, continuous flow-through, computer-operated vermiculture bioreactor for converting organic waste matter into a stable biofertilizer utilizing thermophilic composting and vermicomposting comprising: a decomposing chamber having a first side wall and a second side wall with a release door, a first end wall, a second end wall and a base having a downward slope between the first side wall and a bottom edge of the release door and further comprising aeration ducting to provide oxygen to the organic waste matter; a vermicomposting chamber mounted below the side release door of the decomposing chamber having four side walls and a porous bottom surface; a plurality of sensors for environmental monitoring of the bioreactor and the organic waste matter; a computer-implemented system comprising: a digital processing device comprising: at least one processor, an operating system configured to perform executable instructions, a memory, and a computer program including instructions executable by the digital processing device configured to interface with and control the bioreactor, bioreactor sub-components and the sensors, and communicate with remote monitoring facilities and/or take advantage of cloud computing and storage with a receiver/transmitter device; wherein the decomposing chamber is configured for thermophilic composting to substantially eliminating pathogens from the organic waste matter; begin degrading the lignin with controlled thermophilic heating and cooling, making it palatable for annelids in the vermicomposting chamber, wherein the vermicomposting chamber is configured to receive the substantially pathogen-free decomposed organic waste matter from the decomposing chamber and house a plurality of annelids selected to consume the organic waste matter, converting it to biofertilizer, wherein the plurality of sensors interface and communicate with the computer-implemented system to provide real-time environmental data about the organic waste matter, and wherein the computer-implemented system collects and reports environmental data and controls automated operation of a plurality of mechanical and electrical functions associated with the bioreactor or sub-components thereof. In any embodiment of the bioreactor system, the computer-implemented system further comprises the ability to take advantage of cloud computing and storage of data.

In any embodiment, the aeration ducting comprises perforated ducting connected to an air pump and valving configured to force air through the decomposing chamber for aeration.

In any embodiment, the decomposing chamber further comprises a temperature control system comprising at least one of: a vented ducting arrangement, valving and a pump for forced air infusion, a closed ducting arrangement, valving and a pump for water cooling; a closed ducting arrangement, valving and a pump for refrigerant-type cooling; a turning system to disrupt the organic waste matter; an infrared heating system; a closed ducting arrangement, valving and pump for water heating; an electric coiled system for heating; and a gas burner system for heating.

In any embodiment, the bioreactor further comprises at least one high-torque stepper motor, at least one motor controller and at least one relay to drive any one of a plurality of pumps and valving.

In any embodiment, the bioreactor further comprises injectors in the decomposing chamber connected to a pump and valving configured to add water to the decomposing organic waste matter to ensure that adequate moisture is maintained throughout the composting process.

In any embodiment of the decomposing chamber 110, the slope of the base 105 is about 30°. In some embodiment, the downward slope of the base 105 is equal to or greater than about 30°. In some embodiments, the downward slope of the base 105 is equal to or less than about 30°.

However, depending on the lubricity of the sloped surface, in any embodiment, the slope of the base can have a range anywhere between about 10.0° and about 60.0°. In some embodiments, the slope of the base is: 7.5°, 10.0°, 12.5°, 15.0°, 17.5°, 20.0°, 22.5° 25.0°, 27.5°, 30.0°, 32.5°, 35.0°, 37.5°, 40.0°, 42.5°, 45.0°, 47.5°, 50.0°, 52.5°, 55.0°, 57.5° or 60.0°.

In any embodiment, the plurality of sensors comprise at least one of: a temperature sensor; a relative humidity sensor, a moisture sensor, a chemical sensor, an $O_2$ sensor, a $N_2$ sensor, a $CO_2$ sensor and a pH sensor.

In any embodiment, the bioreactor further comprises a plurality of inoculating pumps and valving configured to inoculate both the decomposing chamber and the vermicomposting chamber with a plurality of microbial inoculum, hormones and nutrients.

In any embodiment, the microbial inoculua of the decomposing chamber comprise lignin-degrading fungi and bacteria.

In any embodiment, the fungi comprise at least one of: arbuscular mycorrhiza fungi (AMF); *Trametes versicolor; Phanerochaete chrysosporium; Basidiomycetes; Ascomycetes*; and *Deuteromycetes*.

In any embodiment, the bacteria comprise at least one of: *Pseudomonas; Flavobacterium*; filimentous bacteria or Actinomycetes and *Thermus* bacteria.

In any embodiment, the microbial inoculua of the vermicomposting chamber comprise microbes beneficial to plant use and can perform at least one of the following functions: promote nutrient acquisition; promote plant growth; promote plant health; promote disease prevention; promote drought resistance; promote insect resistance and kill insects.

In any embodiment, the beneficial microbes comprise at least one of: rhizobia; blue-green cyanobacteria and arbuscular mycorrhiza fungi (AMF).

In any embodiment, the nutrients comprise at least one of: calcium carbonate; magnesium; crushed limestone; carbon; urea; potassium; phosphorous and nitrogen.

In any embodiment, the hormones of the vermicomposting chamber comprise at least one of: Indole-3-acetic acid; gibberellic acid; auxins; cytokinins; gibberellins; abscisic acid and ethylene.

In any embodiment, the vermicomposting chamber further comprises a cutting bar configured to periodically traverse the length of the chamber, near the bottom, to encourage the processed biofertilizer to fall through the porous bottom surface.

In any embodiment, the bioreactor further comprises a solar panel and DC battery power system.

In any embodiment, the bioreactor further comprises a power bank to store energy and perform step-down voltage requirements.

In any embodiment, the power system comprises two or more solar panels.

In any embodiment, the DC battery comprises a deep-cycle battery.

In any embodiment, the plurality of annelids comprise at least one of: *Eisenia fetida* and *Eisenia hortensis*.

In any embodiment, the stable biofertilizer generated therein comprises a carbon to nitrogen ratio of less than 25 parts carbon to 1 part nitrogen.

In any embodiment, the stable biofertilizer generated therein comprises no outright risk of phytotoxicity.

In any embodiment, the stable biofertilizer generated therein comprises no outright risk to human health in the form of organisms that cause human diseases.

In any embodiment, the bioreactor further comprises a locking mechanism capable of closing the release door and configured to assure closure against soft and/or friable debris that may obstruct the door after allowing the organic waste matter to pass between the decomposing chamber and vermicomposting chamber.

In any embodiment, the bioreactor further comprises at least one auger-type mechanism.

In any embodiment, the bioreactor further comprises a high-torque stepper motor, motor controller and relay to drive the at least one auger-type mechanism.

In any embodiment, a movement of the organic waste matter through the bioreactor is accomplished via the at least one auger-type mechanism. This at least one auger-type mechanism can be any form of known auger-type mechanism utilized as a conveyance means to move (typically granular and slurry) materials.

In some embodiments, the high-torque stepper motor, motor controller and relay are interfaced with the auger-type mechanism and the computer-implemented system.

In any embodiment, the locking mechanism is an auger-type locking mechanism.

In any embodiment, the bioreactor further comprises a high-torque stepper motor, motor controller and relay to drive the auger-type locking mechanism.

In any embodiment, a movement of the organic waste matter through the bioreactor is accomplished via gravity.

In any embodiment of the bioreactor, the perforated ducting comprises at least one of: PVC piping; stainless steel piping; rubber tubing and plastic tubing.

In any embodiment of the bioreactor, the porous bottom surface comprises at least one of: a screen; a wire mesh; a grid: straining surface and a sieve.

In any embodiment of the bioreactor, the porous bottom surface has a plurality of sieve or mesh openings having a size of about 1.0 inch (25.4 mm).

In any embodiment of the bioreactor, the porous bottom surface has a plurality of sieve or mesh openings having a size between about 4.0 inches (101.6 mm) or smaller and about 0.158 inch (4.0 mm) or greater.

In any embodiment, the bioreactor further comprises a removable receptacle for capturing the stable biofertilizer dropping through the porous bottom surface.

In any embodiment of the bioreactor, the bioreactor is configured to control the temperature of the organic matter such that it will reach a thermophilic temperature greater than at least about 50° C. (122° F.) but less than about 76° C. (169° F.), for a minimum period of time necessary to substantially render any pathogens harmless to humans before further allowing the organic waste matter temperature to drop to an ambient temperature at a natural thermophilic rate.

In any embodiment of the bioreactor, the bioreactor is configured to control the temperature of the organic matter such that it will reach a thermophilic temperature of greater than at least about 55° C. (131° F.) but less than about 76° C. (169° F.).

In any embodiment of the bioreactor, the organic waste matter temperature is prevented from exceeding a maximum thermophilic temperature with the temperature control system.

In any embodiment of the bioreactor, an ambient temperature of the organic waste matter in the vermiculture chamber is controlled between about 10° C. (50° F.) and about 29° C. (84° F.).

In any embodiment of the bioreactor, the ambient temperature of the organic waste matter in the vermiculture chamber is controlled by the temperature control system.

In any embodiment of the bioreactor, the temperature control system comprises at least one of: a vented ducting arrangement, valving and a pump for forced air infusion; a closed ducting arrangement, valving and a pump for water cooling; a closed ducting arrangement, valving and a pump for refrigerant-type cooling; an automated turning systems to disrupt the organic waste matter; an infrared system; closed ducting arrangement, valving and pump for water heating; an electric coiled system for heating and a gas burner system for heating.

In any embodiment of the bioreactor system, the computer-implemented system further comprises the ability to take advantage of cloud computing and storage of data.

In any embodiment of the bioreactor system herein, the computer-implemented system further comprises the use of machine learning or AI (artificial intelligence) capable of assimilating thousands or even millions of data points acquired by strategically placed sensors placed in and around the bioreactor during the course of converting raw organic waste matter into a stable biofertilizer utilizing thermophilic composting and vermicomposting.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A is a non-limiting isometric view of one embodiment of an auger locking mechanism in an engaged (locked) position on the side door of the thermophilic decomposing chamber.

FIG. 6B is a non-limiting isometric view of one embodiment of an auger locking mechanism in an open (unlocked) position on the side door of the thermophilic decomposing chamber.

FIG. 6C is a non-limiting side view of one embodiment of an auger mechanism capable of performing as a locking mechanism or as a material conveyance mechanism to transfer material between chambers of the bioreactor.

Figure 1:
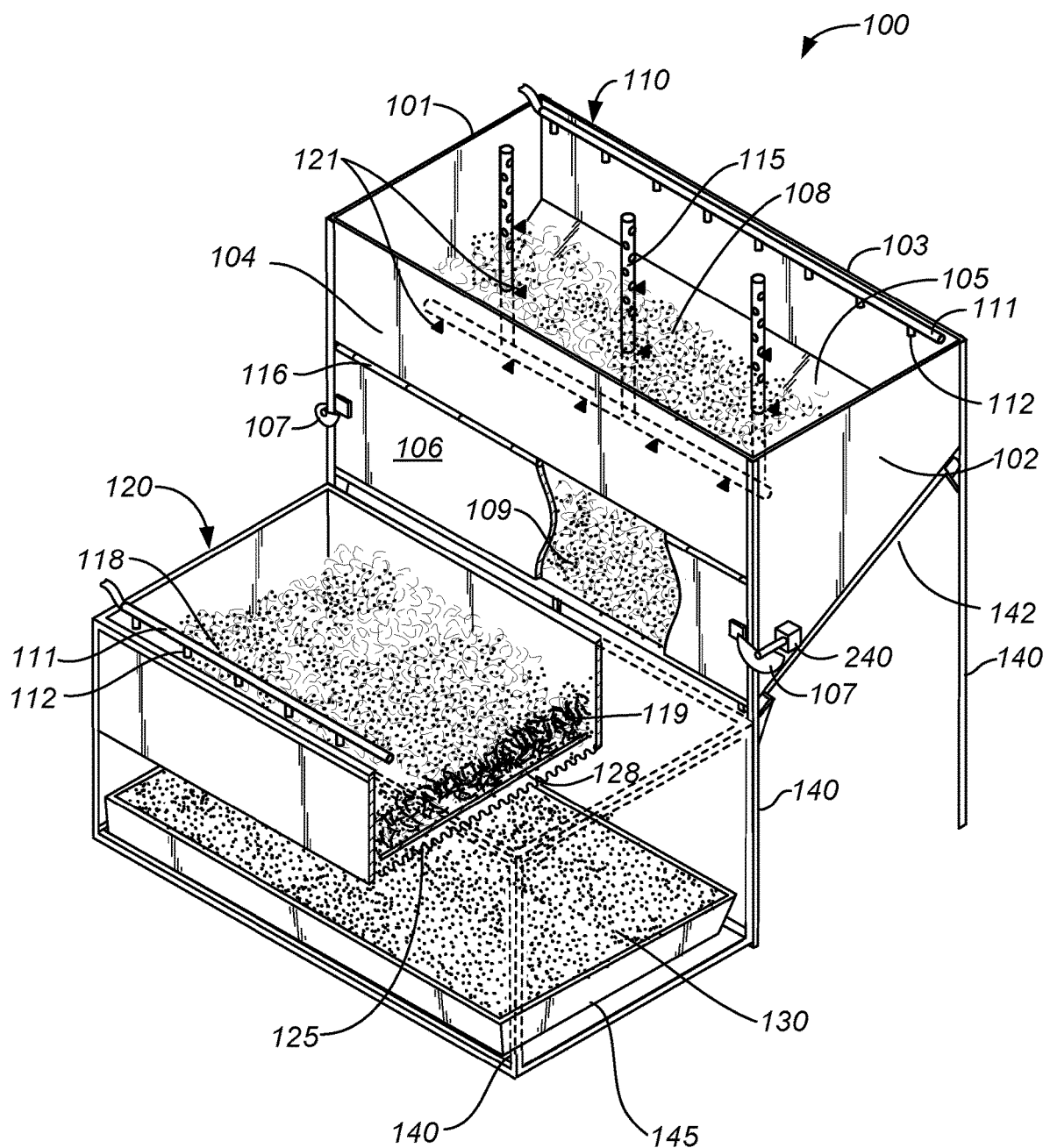
FIG. 1 is a non-limiting isometric view of one embodiment of the bioreactor.

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

DETAILED DESCRIPTION OF THE INVENTION

Provided herein is a portable, climate-controlled, continuous flow-through, computer-operated vermiculture bioreactor and method for the treatment of organic solid wastes utilizing accelerated microbiological decomposition including thermophilic composting and vermicomposting to convert materials into environmentally compatible products, including stable biofertilizer. The portable bioreactor design converts carbon-based organic waste into biofertilizer using thermophilic composting, vermicastings and vermicomposting that can be used directly for plant and farming applications.

In the process of composting, microorganisms break down organic matter and produce carbon dioxide, water, heat, and humus, the relatively stable organic end product. Under optimal conditions, composting proceeds through three phases: 1) the mesophilic, or moderate-temperature phase, which commonly lasts for a couple of days; 2) the thermophilic, or high-temperature phase, which can last from a few days to several months, and finally; 3) a cooling and maturation phase which can last up to several months.

There is a significant difference between a backyard composter and a municipal composter. Municipal composters handle large batches of organic materials all at once, while backyard composters continuously produce a small amount of organic material every day, including animal manure and human waste. Municipal composters, therefore, are "batch" composters, while backyard composters tend to be "continuous" "humanure" composters. When organic material is composted in a batch (municipal), four stages of the composting process are apparent. Although the same phases occur during continuous (humanure) composting, they are not as apparent as they are in a batch, and, in fact, they may be occurring concurrently rather than sequentially.

The four "batch" (municipal) phases include: 1) the mesophilic phase; 2) the thermophilic phase; 3) the cooling phase; and 4) the curing phase.

Stage 1: The Mesophilic Phase: Compost bacteria combine carbon with oxygen to produce carbon dioxide and energy. Some of the energy is used by the microorganisms for reproduction and growth, the rest is given off as heat. When a pile of organic refuse begins to undergo the composting process, mesophilic bacteria proliferate, raising the temperature of the composting mass up to 44° C. (111° F.). This is the first stage of the composting process. These mesophilic bacteria can include *E. coli* and other bacteria from the human intestinal tract, but these soon become increasingly inhibited by the temperature, as the thermophilic bacteria take over in the transition range of 44° C.-52° C. (111° F.-125.6° F.).

Stage 2: The Thermophilic Phase: This begins the second stage of the process, when thermophilic microorganisms are very active and produce a lot of heat. This stage can then continue up to about 70° C. (158° F.), although such high temperatures are neither common nor desirable in backyard compost. This heating stage takes place rather quickly and may last only a few days, weeks, or months. It tends to remain localized in the upper portion of a backyard compost bin where the fresh material is being added, whereas in batch compost, the entire composting mass may be thermophilic all at once.

Stage 3: The Cooling Phase: After the thermophilic heating period, the humanure will appear to have been digested, but the coarser organic material will not. This is when the third stage of composting, the cooling phase, takes place. During this phase, the microorganisms that were chased away by the thermophiles migrate back into the compost and get back to work digesting the more resistant organic materials. Fungi and macroorganisms such as earthworms and sowbugs that break the coarser elements down into humus also move back in.

After the thermophilic stage has been completed, only the readily available nutrients in the organic material have been digested. There's still a lot of food in the pile, and a lot of work to be done by the creatures in the compost. It takes many months to break down some of the more resistant organic material in compost such as "lignin" which comes from wood materials. Like humans, trees have evolved with a skin that is resistant to bacterial attack, and in a compost pile those lignins resist breakdown by thermophiles. However, other organisms, such as fungi, can break down lignin, given enough time; since they don't tolerate the heat of thermophilic compost, they simply wait for things to cool down before beginning their job.

Stage 4: The Curing Phase: The final stage of the composting process is called the curing, aging, or maturing stage, and it is a long and important one. Commercial composting professionals often want to make their compost as quickly as possible, usually sacrificing the compost's curing time. It has been noted that if municipal/commercial composters could shorten their compost time to four months, they could make three batches of compost a year instead of only the two they typically produce, thereby increasing their output by 50%. Municipal composters see truckloads of compost coming in to their facilities daily, and they want to make sure they don't get inundated with organic material waiting to be composted. Therefore, they feel a need to move their material through the composting process as quickly as possible to make room for the new material coming in. Household composters don't have that problem, although many backyard composters also wish to make compost as quickly as possible. However, the curing, aging, or maturing of the compost is a critically important stage of the compost-making process. And, as in wine-making, patience is critical.

A long curing period (e.g., up to a year after the thermophilic stage in some composting processes) adds a safety net for pathogen destruction. Many human pathogens only have a limited period of viability in the soil, and the longer they are subjected to the microbiological competition of the compost pile, the more likely they will die a swift death.

Immature compost can be harmful to plants. Uncured compost can produce phytotoxins (substances toxic to plants), can rob the soil of oxygen and nitrogen and can contain high levels of organic acids.

Different communities of microorganisms predominate during the various composting phases. Initial decomposition is carried out by mesophilic microorganisms, which rapidly break down the soluble, readily degradable compounds. The heat they produce causes the compost temperature to rapidly rise. As the temperature rises above about 40° C., the mesophilic microorganisms become less competitive and are replaced by others that are thermophilic, or heat-loving. At temperatures of roughly 50° C.-55° C. and above, many microorganisms that are human or plant pathogens are destroyed. Because temperatures over about 65° C. kill many forms of microbes and limit the rate of decomposition, compost managers use aeration and mixing to keep the temperature below this point.

During the thermophilic phase, high temperatures accelerate the breakdown of proteins, fats, and complex carbohydrates like cellulose and hemicellulose, the major structural molecules in plants. As the supply of these high-energy compounds becomes exhausted, the compost temperature gradually decreases and mesophilic microorganisms once again take over for the final phase of "curing" or maturation of the remaining organic matter.

Thermophilic composting is the practice of breaking down biological waste such as proteins, fats, and complex carbohydrates, as noted above with thermophilic (heat-loving) bacteria. Thermophilic composting is distinct from vermicomposting (which uses worms). As a general rule, thermophilic compost heaps must be quite large; typically 1 m³ or larger. Commonly, carbon based organic materials such as grass cuttings, wood chips and sawdust should be put into thermophilic compost heaps. Food scraps are more suited to vermicomposting. Worms are unique to the process of composting and are distinguished from the other decomposers such as bacteria and fungi which are unable to ingest discrete lumps of matter such as worms do, but instead live by absorbing and metabolizing on a molecular scale. Worms obtain nutrients by consuming detritus (decomposing plant and animal parts, as well as organic fecal matter).

The key advantage of thermophilic composting is that the high temperatures kill diseases. Human feces composted by worms is not safe to use on food-plants, but adequate time and temperature in a thermophilic composting process will render it quite harmless and an excellent farming fertilizer.

The key advantage of vermicomposting composting WITH thermophilic composting is that the end-product results in a product that is of superior quality in terms of stability as well as Nitrogen, Phosphorous and Carbon content. In addition, pre-composting with thermophilic composting methods reduces the time required to achieve a stable vermicompost. The literature clearly suggests that vermicompost systems produce a greater variety of phytohormones while compost contains slightly greater amounts of mineral nutrients. This is presumably due to reduced leaching during the composting process compared to vermicomposting.

Further still, the resulting compost end product produced with this system is provided with real-time data as to its nutrient make-up, and requires less (human) effort and time to maintain due to the computer operated and controlled components.

Temperature:

All the organisms that cause human diseases are adapted to live around human body temperature. Higher temperatures kill them. Compost that stays at or above 50° C. (122° F.) for 24 hours will be safe to use to grow food. A temperature of 46° C. (115° F.) will kill pathogens within a week. 62° C. (143.6° F.) will kill pathogens in one hour.

The bacteria that make compost need oxygen. Typical thermophilic compost heaps can be aerated by sticking holes in the heap with pipes or sticks. Optionally, coarse materials like hay can be interspersed throughout the compost when building the compost heap, to create little pockets of air. However, frequent turning or manual aeration of the compost heap is generally needed to maintain the process in a steady manner.

A hot compost pile is meant to get hot, but too much heat is detrimental to the process. This heat is generated not from the sun but rather is the by-product of microbial life. Their eating, movement, and reproduction all cause heat too build-up and when the proper conditions are present, the compost pile heats up accordingly. In common thermophilic composting heaps, temperatures should reach 160 F (72 C) but not go any higher. Composters know that when a heap is approaching these temperatures, it's time to aerate or flip the pile.

If it goes higher than 160 F (72 C), there is a small window where facultative anaerobes will proliferate, as the pile swings from aerobic to anaerobic at this edge. (Edges are places of varied ecology as they share resources between two distinct ecosystems and acre known as a net and sieve for energy. One can increase the yield of the system by manipulating where two ecosystems meet, and designing in their unique species. Edge is a multi-dimensional element that encompasses space and time giving rise to the dynamic interplay between life and death itself. Whether it is shredding organic material, giving it a greater surface area for microbes to inhabit, or our stomachs sinuous path to increase digestive capability, nature employs its intelligence through this principle). Once above this threshold, the pile will go anaerobic and piles that are too high in nitrogen have actually been known, although rare, to actually catch fire. Typical thermophilic compost heaps will have warmth to them for around 35 days and getting them above 130° F. helps to kill pathogens and weed seeds. If the typical thermophilic compost heap spikes to 160 F or 70 C within one or two days, it is likely due to excessive nitrogen and will require near daily turning and can lead to anaerobic piles. A well-balanced thermophilic compost heap should get to that peak temperature in day three or four. However, if the typical thermophilic compost heap doesn't heat it could be from not enough green material or insufficient water content.

As noted above, improper moisture levels or water content can retard the thermophilic composting process. The moisture level of the typical thermophilic compost heap should be between 35 and 60 percent; which this can be calculated scientifically, but essentially means the pile should feel evenly moist, but not soggy. The more air that can be incorporated into the pile, the better. The typical thermophilic compost heap can be mixed by hand, but using a lot of "fluffy" materials, like grass clippings, provides ample air space to balance out the thick sludge formed by decomposing food scraps. This point speaks to the correct carbon-to-nitrogen ratio, as well. Food scraps have a relatively high nitrogen content and need to be balanced with materials rich in carbon, like dry leaves or straw. The typical thermophilic compost heap ratio is about 30 parts carbon to 1 part nitrogen.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "natural thermophilic rate" and similar terms refers to a state of composting wherein "the rate at which labile carbon is consumed" or "the rate at which heat is naturally dissipated as a result of the decline in microbial respiration". Labile organic carbon is the portion of soil organic carbon that can be readily decomposed by soil organisms. Farm productivity is closely linked to soil functions that depend on the amount and quality of labile organic carbon, and its turnover rate.

As used herein the term "injectors", "sprayers", "sprinklers" and similar terms refer to any apparatus or sub-assembly within the bioreactor responsible for inserting, injecting or spraying an additive into the composting material of the bioreactor. Common additives include water, lignin-degrading fungi and bacteria, microbes, nutrients and hormones beneficial to plant use.

As used herein the phrase "an acceptable state of thermophilic composting" and similar phrases refers to a state of composting at the end of the second stage of composting (thermophilic phase), and just prior to the beginning of the third stage of composting (cooling phase), where the microorganisms that were chased away by the thermophiles (thermophilic microorganisms) migrate back into the compost and get to work digesting the more resistant organic materials. During the cooling phase, fungi and macroorganisms such as earthworms and sowbugs break the coarser elements down into humus.

As used herein the term "valve", "valves", "valving" and similar terms refer to any device for halting or controlling the flow of a liquid, gas or other material through a passage, pipe, duct, inlet, outlet or other means of conveyance or transport therefor. Valves are commonly associated with systems utilizing pumps and similar apparatus utilized for raising, driving, exhausting or compressing fluids or gasses, usually by means of a piston, plunger or set of rotating vanes.

Digital Processing Device

In some embodiments, the bioreactor system described herein includes a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein. In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the bioreactor system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the bioreactor system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® Actionscript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-In

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called micro-browsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the bioreactor system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the bioreactor system disclosed herein includes one or more databases, or use of the same. In view of the disclosure provided herein, those of skill in the art will recognize that many databases are suitable for storage and retrieval of bioreactor, bioreactor sub-components and sensor information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Machine Learning and Artificial Intelligence (AI) System

In any embodiment of the bioreactor system herein, the computer-implemented system further comprises the use of machine learning or AI (artificial intelligence) capable of assimilating thousands or even millions of data points acquired by strategically placed sensors placed in and around the bioreactor during the course of converting raw organic waste matter into a stable bio fertilizer utilizing thermophilic composting and vermicomposting.

The AI system herein comprises various sensors and circuit boards that optionally include a digital processor (such as a Raspberry Pi [a series of credit card-sized single-board computers), or Arduinos (an open-source prototyping platform), as non-limiting examples, that either through wifi, radio frequency, wires, or other mechanism communicate to a server that can store data in the cloud, or a hard drive, or in a data historian. Humans may play some role in the form of gathering, analyzing, or manipulating this data.

With environmental data such as oxygen levels, humidity, temperature, airflow etc. and other data points, the learning possibilities are expanded significantly. Compounding this data within improved horticultural knowledge makes it possible to improve and optimize the conversion process.

Those of skill will recognize that the various illustrative logical blocks, modules, circuits, and algorithm steps described in connection with the embodiments disclosed herein, including with reference to the control systems described herein, for example, may be implemented as electronic hardware, software stored on a computer readable medium and executable by a processor, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. For example, various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a Raspberry PI further comprising Arduinos, a plurality of microprocessors, one or more microprocessors in conjunction with a DSP core, or any other such configuration. Software associated with such modules may reside in RAM memory, flash memory, ROM memory, EPROM memory, EEPROM memory, registers, a hard disk, a removable disk, a CD-ROM, or any other suitable form of storage medium known in the art. An exemplary storage medium is coupled to the processor such the processor can read information from, and write information to, the storage medium. In the alternative, the storage medium may be integral to the processor. The processor and the storage medium may reside in an ASIC. For example, in one embodiment, a controller for use of control of the IVT comprises a processor (not shown).

Vermiculture Bioreactor

As illustrated in FIGS. 1, 1A, 2, 3, 4, 5 and 6A-6C, provided herein is a portable, climate-controlled, continuous flow-through, computer-operated vermiculture bioreactor 100 for converting organic waste matter into a stable biofertilizer utilizing thermophilic composting and vermicomposting comprising: a decomposing chamber 110 having a first side wall 103 and a second side wall 104 with a release door 106, a first end wall 101, a second end wall 102 and a base 105 having a downward slope between the first side wall and a bottom edge of the release door (a) and further comprising aeration ducting 115 to provide oxygen to the raw organic waste matter 108; a vermicomposting chamber 120 mounted below the side release door 106 of the decomposing chamber 110 having (four) side walls and a porous bottom surface 125; a plurality of sensors 121 for environmental monitoring of the bioreactor and the organic waste matter; a computer-implemented system 300 comprising: a digital processing device 260 comprising: at least one processor 2601, an operating system 2602 configured to perform executable instructions, a memory 2603, and a computer program 2604 including instructions executable by the digital processing device configured to interface with and control the bioreactor, bioreactor sub-components and the sensors 121, and communicate with remote monitoring facilities 280, and/or take advantage of cloud computing 290 and storage through any common form of communication, with a receiver/transmitter device 2605 which include, by way of non-limiting examples, direct (hard wired) communication means, cellular, Wifi, an Intranet, the Internet, Bluetooth® or other wireless technology and the cloud; wherein the decomposing chamber 110 is configured for thermophilic composting to substantially eliminating pathogens from the raw organic waste matter; begin degrading the lignin with controlled thermophilic heating (and cooling as needed), making it palatable for annelids 119 in the vermicomposting chamber 120, wherein the vermicomposting chamber is configured to receive the substantially pathogen-free, partially decomposed organic waste matter 109 from the decomposing chamber which is now referred to as "cooled" thermophilically composted organic waste 118 and house a plurality of annelids 119 selected to consume the organic waste matter 118, converting it to biofertilizer 130, wherein the plurality of sensors 121 interface and communicate with the computer-implemented system 300 to provide real-time environmental data about the organic waste matter, and wherein the computer-implemented system collects and reports environmental data and controls automated operation of a plurality of mechanical and electrical functions associated with the bioreactor or sub-components thereof. In any embodiment of the bioreactor system, the computer-implemented system further comprises the ability to take advantage of cloud computing and storage of data.

Figure 2:
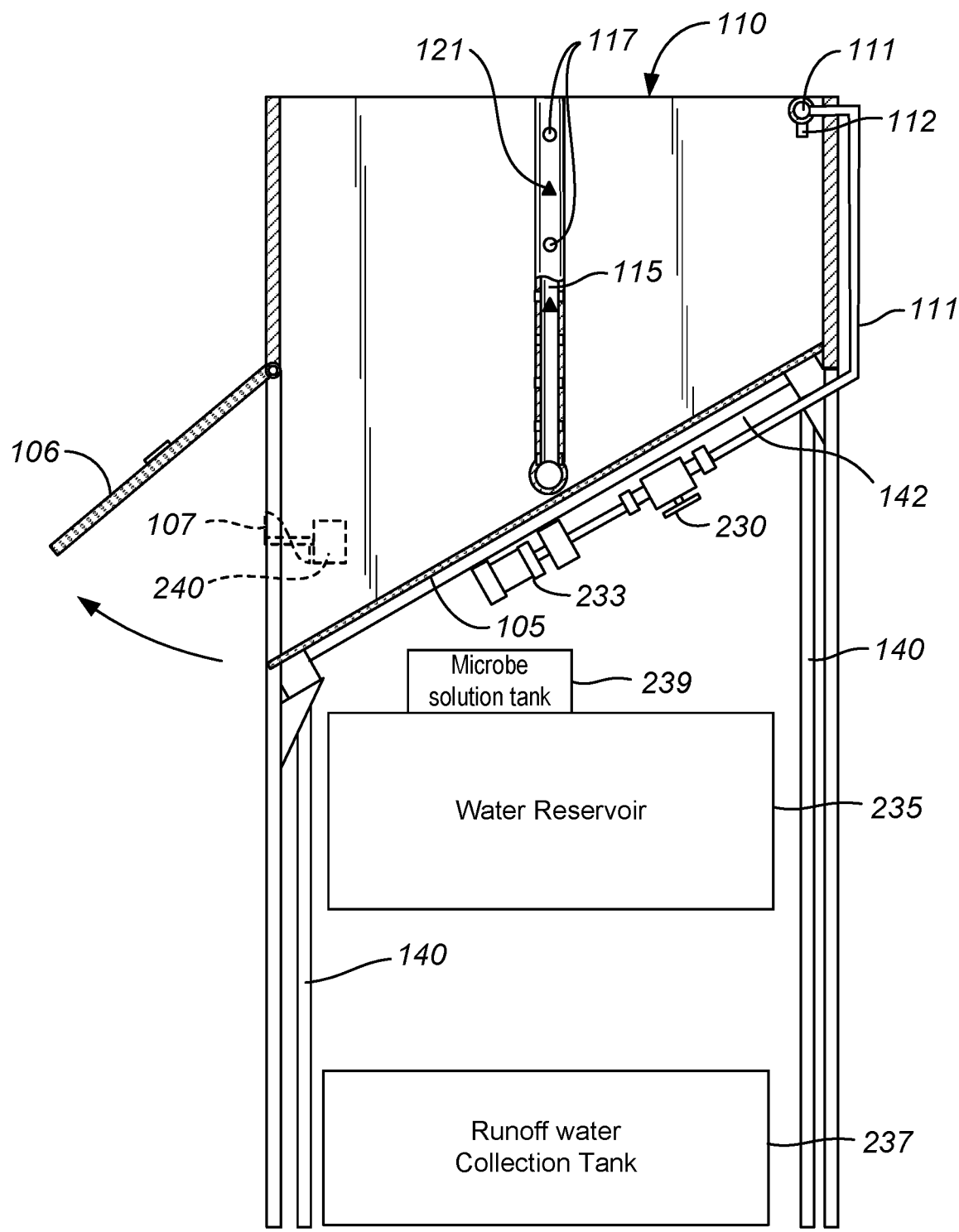
FIG. 2 is a non-limiting cross-sectional view of one embodiment of the thermophilic decomposing chamber of the bioreactor and corresponding reservoirs for water, microbes and nutritional additives.
Figure 3:
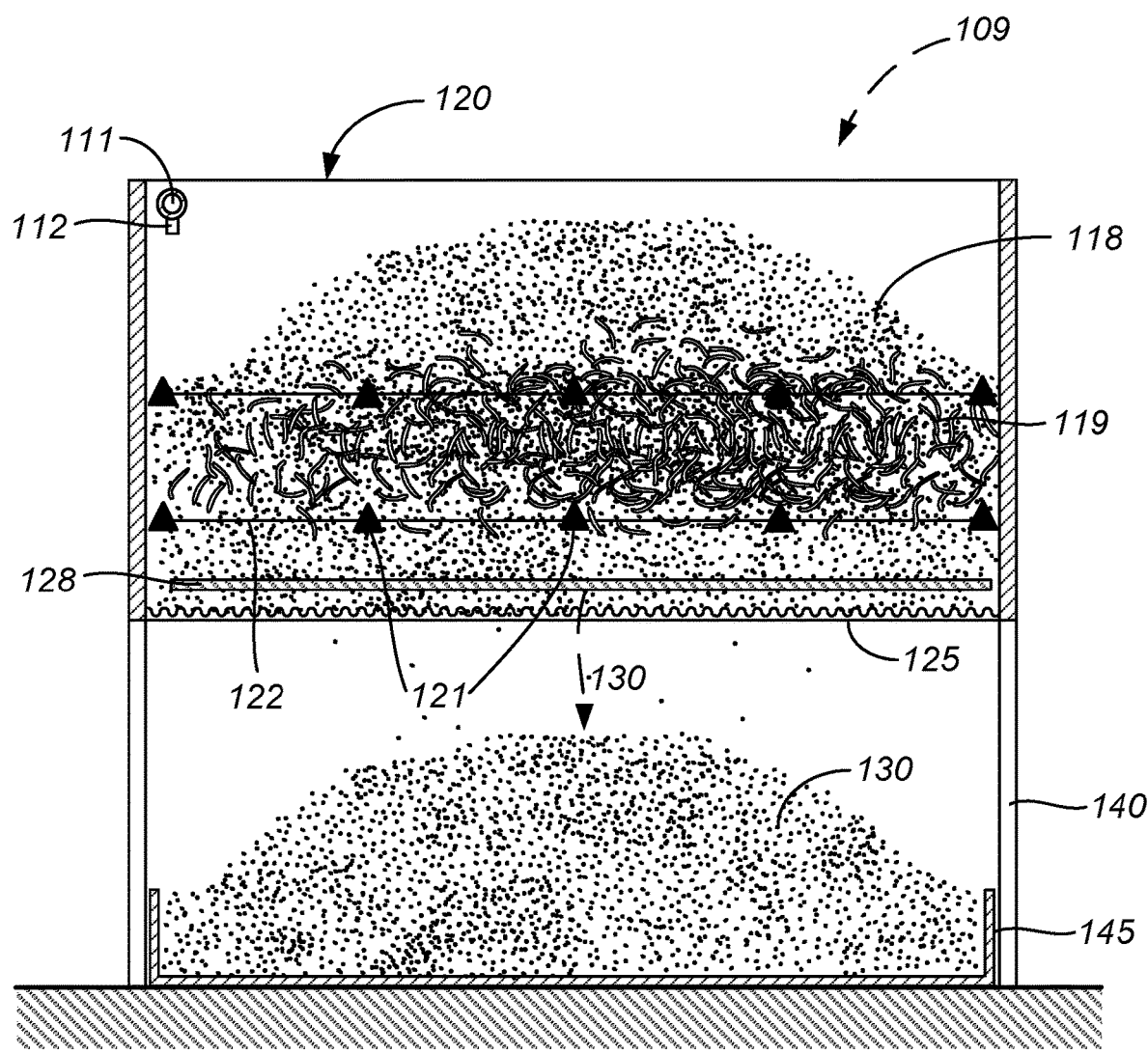
FIG. 3 is a non-limiting cross-sectional view of one embodiment of the vermiculture chamber and bio fertilizer receptacle of the bioreactor.

In any embodiment of the bioreactor, the sensors 121 may be configured for hard-wired or wireless communication with the computer-implemented operating system. As illustrated in FIG. 3, the sensors 121 may be hardwired 122. As illustrated in FIGS. 1 and 2, the sensors 121 may be configured for wireless communication.

In any embodiment of the bioreactor, the perforated ducting comprises at least one of: PVC piping; stainless steel piping; rubber tubing and plastic tubing.

The aeration ducting 115, as illustrated in FIGS. 1 thru 3, comprises perforated ducting connected to an air pump 233 and valving 230 configured to force air through the decomposing chamber 110 for aeration as part of the thermophilic or high temperature phase, to maintain and assure aerobic decomposition conditions within the chamber.

In any embodiment of the decomposing chamber 110, the bioreactor system electrical assembly 201 further comprises a temperature control system 225 comprising at least one of: a vented ducting arrangement, valving and a pump for forced air infusion, (such as that illustrated in FIGS. 1 and 2), a closed ducting arrangement, valving and a pump for water cooling; a closed ducting arrangement, valving and a pump for refrigerant-type cooling; a turning system to disrupt the organic waste matter; an infrared heating system; a closed ducting arrangement, valving and pump for water heating; an electric coiled system for heating; and a gas burner system for heating.

In any embodiment, the plurality of sensors 121 comprises at least one of: a temperature sensor; a relative humidity sensor, a moisture sensor, a chemical sensor, an $O_2$ sensor, a $N_2$ sensor, a $CO_2$ sensor and a pH sensor.

In any embodiment of the bioreactor system, the plurality of sensors 121 may interface with the computer-implemented.

In one embodiment, the sensors 121 are positioned along the aeration ducting 115, interspersed between and away from the perforations or air jets 117 in the aeration ducting in order to avoid the potential for the airflow from the perforations or air jets causing any disruption in the sensor readings. Alternately, the sensors could be placed anywhere in the decomposing chamber where they would be exposed to the decomposing organic waste matter. Depending on the information sought, the sensors may each be strategically placed to optimize the information sought. As a non-limiting example, a temperature sensor and a relative humidity sensor may be placed in the chamber above the decomposing organic waste matter. Whereas, a moisture sensor, a chemical sensor, an $O_2$ sensor, a $N_2$ sensor, a $CO_2$ sensor and a pH sensor may all be placed such that they are in direct contact with the decomposing organic waste matter, at or near the side release door.

Further, the sensors are programmable. Readings from the sensors can be adjusted to within a broad range between continuous monitoring, monitoring every few seconds, every few minutes, hourly, every few hours, daily and weekly readings.

In one embodiment, the sensors 121 would be set up to take readings every 5-10 minutes to help conserve battery life. However, the iteration for sensor reading would need to coincide with the efficiency of the power source.

Figure 4:
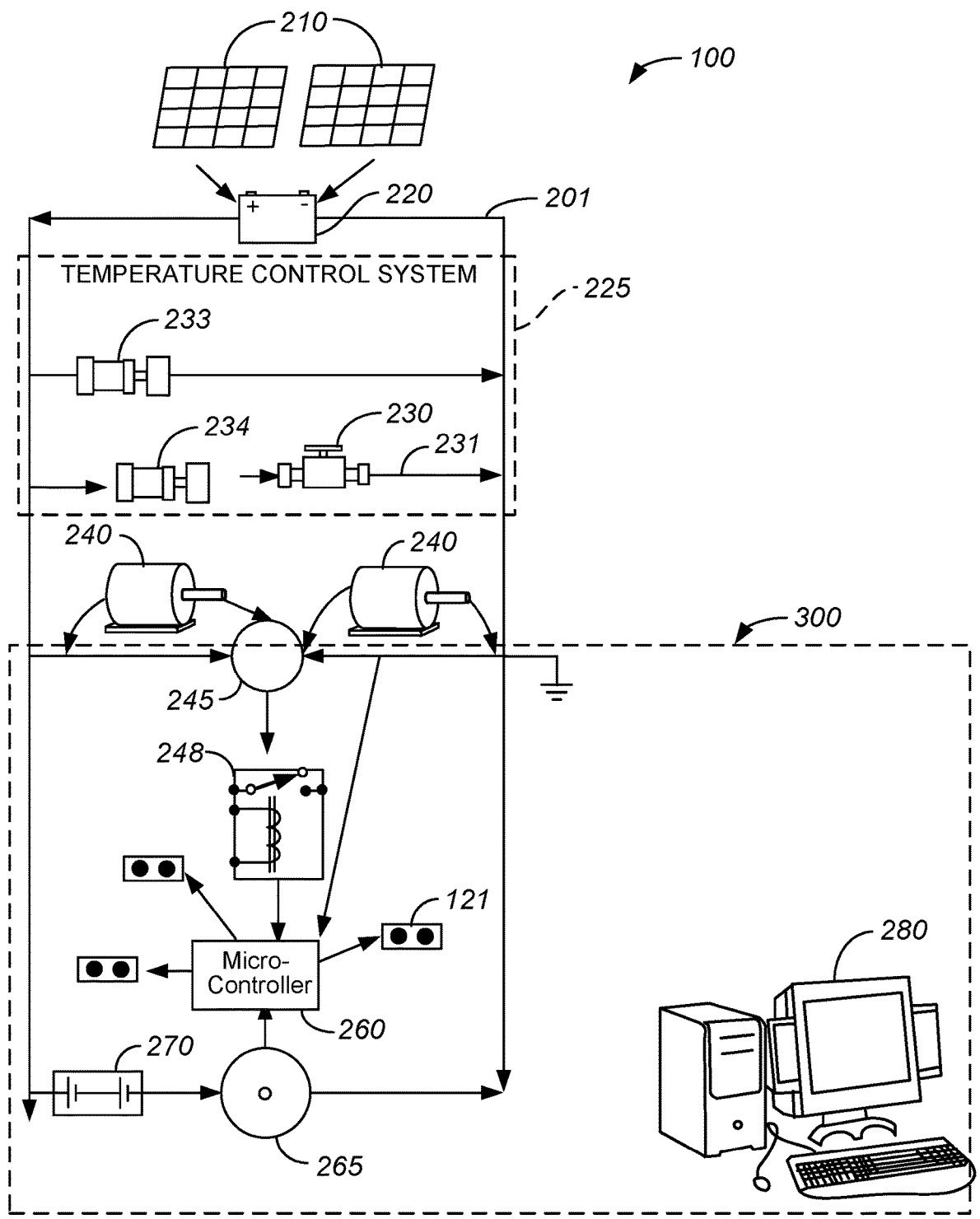
FIG. 4 is a non-limiting electrical diagram schematic and pictorial representation of the remote monitoring system of the bioreactor system.

As illustrated in FIG. 4, in any embodiment, the bioreactor system 100 further comprises at least one solar panel 210 and DC battery power system 220.

In any embodiment, the bioreactor further comprises a power bank 270 to store energy and perform step-down voltage requirements.

In any embodiment, the power system comprises two or more solar panels 210.

In any embodiment, the DC battery comprises at least one deep-cycle battery 220.

In the present embodiment, the system is configured for self-sufficient, independent operation, off the power grid. Efficiency of the solar panels 210 and their ability to efficiently recharge the deep-cycle DC batteries 220 would be a contributing factor to the rate of sensor readings.

In another embodiment, the system is configurable for hybrid operation, utilizing the power grid to supply power for daily operations of the system and to recharge batteries when there is inadequate energy available from alternate non-grid sources.

In yet another embodiment, the system is configurable for standard 110/120 or 220/240 volt and 60 Hz/50 Hz frequency operation utilizing the power bank 270 to store energy and/or perform step-down voltage requirements, where power supply is not expected to be an issue.

In any embodiment, the bioreactor further comprises injectors 112 in the decomposing chamber connected to a pump 234 and valving 231 configured to add water to the decomposing organic waste matter to ensure that adequate moisture is maintained throughout the composting process.

In any embodiment of the bioreactor 100, the electrical control assembly 201 further comprises at least one high-torque stepper motor 240, at least one motor controller 245 and at least one relay 248 to drive any one of a plurality of pumps 233, 234 and valving 230, 231.

Additionally, the decomposing chamber 110 comprises water piping 111 and injectors 112 for supplying water and injecting a plurality of microbes into the decomposing organic waste matter. Water is supplied to maintain a moisture level within an optimum range between about 50% to about 80% gravimetric moisture during the thermophilic phase in the decomposing chamber. However, once the thermophilic phase is completed (near the bottom of the chamber), when the decomposing organic waste matter begins to enter the cooling phase, the optimum moisture range may be adjusted to between about 40% to about 80%.

The system is configured such that the thermophilic phase of decomposition will last between about 2 weeks to about 3 weeks, depending on the starting composition of the organic waste matter.

The pH range for the organic waste matter changes over time and depends on the waste that is processed. In the thermophilic chamber, the pH can range between 5 and 10, and in the cooling and curing phase in the vermicomposting chamber, the waste will generally be about 0.5 to 1.0 points lower than the initial waste. However, it is important to know what the initial waste pH measures because a pH that is too low may inhibit thermophilic composting which may require the system to pump water or the system manager to add some limestone.

Additionally, $H_2SO_4$ (which can decrease pH) is optionally used as an additive to the fertilizer, as well as blood meal, feather meal, and bone meal which can be used to further improve biofertilizer quality.

The decomposing chamber 110 further comprises a base 105 having a downward slope between the first side wall 103 and a bottom edge of the release door 106(*a*). The decomposing chamber is ideally configured with the downward sloping base to take advantage of gravity in order to move the thermophilically composted organic waste matter from the composing chamber to the vermicomposting chamber.

In any embodiments of the bioreactor system, each chamber of the bioreactor has an approximate capacity of 1.0 m³ or larger. In one embodiment, the decomposing chamber 110 is about six (6.0) feet (1.83 m) long, has a first side wall height of about one (1.0) feet, (0.33 m), and a second side wall height of about three (3.0) feet, (0.914 m), with a 30° sloping base and a level, open top approximately three (3.0) feet, (0.914 m) wide.

In any embodiment of the decomposing chamber 110, the slope of the base 105 is about 30°. In some embodiment, the downward slope of the base 105 is equal to or greater than about 30°. In some embodiments, the downward slope of the base 105 is equal to or less than about 30°.

However, depending on the lubricity of the sloped surface, the slope of the base can have a range anywhere between about 10.0° and about 60.0°. In some embodiments, the slope of the base is: 7.5°, 10.0°, 12.5°, 15.0°, 17.5°, 20.0°, 22.5° 25.0°, 27.5°, 30.0°, 32.5°, 35.0°, 37.5°, 40.0°, 42.5°, 45.0°, 47.5°, 50.0°, 52.5°, 55.0°, 57.5° or 60.0°.

In any embodiment, a movement of the organic waste matter through the bioreactor is accomplished via the at least one auger-type mechanism 243. This at least one auger-type mechanism 243 can be any form of known auger-type mechanism utilized as a conveyance means to move (typically granular and slurry) materials.

In another embodiment, the inventor has envisioned the use of the auger mechanism 243 in the composting chamber that would be engaged to push a portion of the thermophilically composted organic waste matter 109, from the decomposing chamber 110 through the side release door 106, to the vermicomposting chamber 120. In this embodiment, any slope provided in the base would be optional.

In still another embodiment, the inventor has envisioned the use of an auger mechanism 243 in combination with a pusher bar (not shown) positioned along the bottom surface in the decomposing chamber 110 that would be engaged to push a portion of the thermophilically composted organic waste matter 109 from the decomposing chamber 110 through the side release door 106, to the vermicomposting chamber 120. In this embodiment, any slope provided in the base 105 would be optional.

As noted previously, the decomposition chamber further comprises a side release door 106 in the second wall, wherein the bottom edge 106a of the side release door is positioned at the bottom of the downward slope of the base surface 105.

In one embodiment the side release door is approximately ½ the height of the entire $2^{nd}$ side wall, stretching between the first end 101 and the second end 102, and ideally comprises a hinging mechanism 116 allowing it to swing open and closed. However, the actual height is of less importance than the width and can vary substantially between ⅛ and ⅔ the height of the $2^{nd}$ side wall.

In any embodiment, the bioreactor further comprises at least one auger-type mechanism 243. This at least one auger-type mechanism 243 can be any form of known auger-type mechanism utilized as a conveyance means to move (typically granular and slurry) materials.

In any embodiment, the bioreactor further comprises a high-torque stepper motor 240, motor controller 245 and relay 248 to drive the at least one auger-type mechanism 243.

In some embodiments, the high-torque stepper motor 240, motor controller 245 and relay 248 are interfaced with the auger-type mechanism 243 and the computer-implemented system 300.

In any embodiment, the locking mechanism is an auger-type locking mechanism 107.

In any embodiment, the bioreactor further comprises a high-torque stepper motor 240, motor controller 245 and relay 248 to drive the auger-type locking mechanism 107.

In any embodiment of the decomposing chamber 110, opening and closing of the side release door 106 is controlled by a locking mechanism. In one embodiment, the locking mechanism comprises an auger locking mechanism 107. In one embodiment, the auger locking mechanism is located on both sides of the side release door, positioned at a height of about one half the height of the side release door, up from the bottom edge 106a. In one embodiment, the augers are about 6 inches in length with the base of the auger being flush with the side of the door when it is firmly closed. In one embodiment, the augers are attached to the side of the first chamber frame with stepper motors 240 that move the augers in order to open and close the door, as illustrated in FIGS. 1 and 2. The auger locking mechanism is configured to assure closure against soft and/or friable debris that may obstruct the door after allowing the organic waste matter to pass between the decomposing chamber and vermicomposting chamber.

In any embodiment of the bioreactor system, the system further comprises a water reservoir tank 235, to provide moisture to the system.

In any embodiment of the bioreactor system, the system further comprises a plurality of microbe reservoirs 239, to contain a ready supply of the microbial inoculua and nutrients to be utilized by the system during the composting process.

In any embodiment of the bioreactor system, the system further comprises a runoff water collection tank 237, to collect any moisture or excess water runoff produced by the system.

Figure 1A:
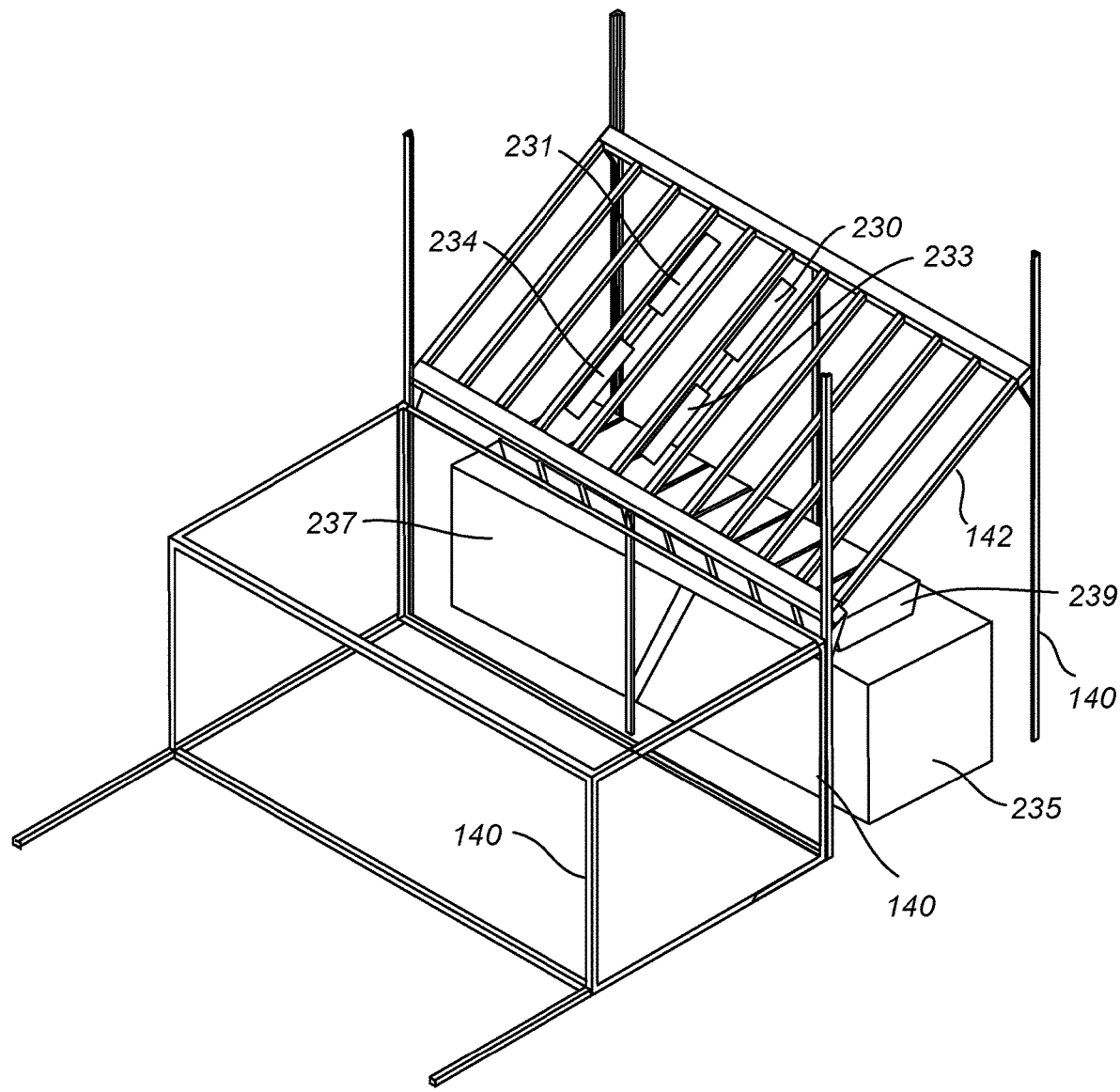
FIG. 1A is a non-limiting isometric view of one embodiment of the structural frame of the bioreactor.

As illustrated in FIGS. 1A and 2, the various reservoirs and collection tanks can be compactly positioned in near proximity to the bioreactor, such as beneath the sloped bottom frame 142 or between the bioreactor frame legs 140. Alternately, these reservoirs and collection tanks can be positioned nearby for easy access and maintenance.

In any embodiment, the bioreactor further comprises a plurality of inoculating pumps 234 and valving 231 configured to inoculate both the decomposing chamber 110 and the vermicomposting chamber 120 with moisture and a plurality of microbial inoculum, hormones and nutrients stored in the water reservoir tank 235 and any of the plurality of microbe reservoirs 239.

In any embodiment, the microbial inoculua utilized in the decomposing chamber comprise lignin-degrading fungi and bacteria.

Bacteria are the smallest living organisms and the most numerous in compost; they make up 80 to 90% of the billions of microorganisms typically found in a gram of compost. Bacteria are responsible for most of the decomposition and heat generation in compost. They are the most nutritionally diverse group of compost organisms, using a broad range of enzymes to chemically break down a variety of organic materials.

The characteristic earthy smell of soil is caused by actinomycetes, organisms that resemble fungi but actually are filamentous bacteria. Like other bacteria, they lack nuclei, but they grow multicellular filaments like fungi. In composting they play an important role in degrading complex organics such as cellulose, lignin, chitin, and proteins. Their enzymes enable them to chemically break down tough debris such as woody stems, bark, or newspaper. Some species appear during the thermophilic phase, and others become important during the cooler curing phase, when only the most resistant compounds remain in the last stages of the formation of humus.

Fungi include molds and yeasts, and collectively they are responsible for the decomposition of many complex plant polymers in soil and compost. In compost, fungi are important because they break down tough debris, enabling bacteria to continue the decomposition process once most of the cellulose has been exhausted. They spread and grow vigorously by producing many cells and filaments, and they can attack organic residues that are too dry, acidic, or low in nitrogen for bacterial decomposition.

In any embodiment, the fungi comprise at least one of: arbuscular mycorrhiza fungi (AMF); *Trametes versicolor; Phanerochaete chrysosporium; Basidiomycetes; Ascomycetes;* and *Deuteromycetes.*

In any embodiment, the bacteria comprise at least one of: *Pseudomonas; Flavobacterium*; filamentous bacteria or Actinomycetes and *Thermus* bacteria.

In any embodiment, the microbial inoculua of the vermicomposting chamber comprise microbes beneficial to plant use and can perform at least one of the following functions: promote nutrient acquisition; promote plant growth; promote plant health; promote disease prevention; promote drought resistance; promote insect resistance and kill insects.

In any embodiment, the beneficial microbes comprise at least one of: rhizobia; blue-green cyanobacteria and arbuscular mycorrhiza fungi (AMF).

In any embodiment, the nutrients comprise at least one of: calcium carbonate; magnesium; carbon; urea; potassium; phosphorous and nitrogen. For the purposes of this application, crushed limestone is particularly useful for improving pH and increasing calcium or magnesium in the end-product.

In any embodiment, the hormones of the vermicomposting chamber comprise at least one of: Indole-3-acetic acid; gibberellic acid; auxins; cytokinins; gibberellins; abscisic acid and ethylene.

As illustrated in FIG. 3, in any embodiment of the bioreactor system, the vermicomposting chamber 120 further comprises a cutting bar 128 configured to periodically traverse the length of the chamber, near the bottom, to encourage the processed biofertilizer 130 to fall through the porous bottom surface 125.

As noted previously, in any embodiment of the bioreactor system, the vermicomposting chamber 120 comprises a plurality of annelids (worms) 119. In any embodiment, the plurality of annelids comprises at least one of the species selected from a group comprising: *Eisenia foetida, Eisenia hortensis* and *Eudrilus eugeniae*. Another known species is *Lumbricus rubellus*. One of skill in the art would recognize that many other species may be suitable for this purpose. Redworms (also known as red wiggler, brandling or manure worms) are often believed to be best suited to worm composting because they thrive on organic material, such as food waste. They are often found in aged manure, compost heaps, and piles of leaves.

In any embodiment, the stable biofertilizer generated therein comprises a carbon to nitrogen ratio of less than 25 parts carbon to 1 part nitrogen.

The carbon to nitrogen ratio (C:N ratio) is generally thought to be relatively flexible when it comes to personal use, having a ratio around 25-30:1 may be good, but much of the literature generally calls for a ratio of 25:1.

In a preferred embodiment of the present invention, the C:N ratio of 25:1 or less is also a good number because the meta-analysis of the final product produced from the present invention found that the C:N ratio of final products generally range from 10:1 to 20:1, so having a ratio of less than 25:1 is reasonable. Additionally, one of the reasons why the C:N ratio for the product produced from the present invention is less than 30 is because the combined thermophilic/vermiculture composting process includes earthworm consumption, (in addition to thermophilic decomposition), which can and does remove additional carbon from the waste, while traditional composting does not.

In any embodiment, the stable biofertilizer generated therein comprises no outright risk of phytotoxicity.

In any embodiment, the stable biofertilizer generated therein comprises no outright risk to human health in the form of organisms that cause human diseases.

The key advantage of thermophilic composting is that the high temperatures kill diseases. Human feces composted by worms alone is not safe to use on food-plants, but several months of thermophilic composting in a typical residential composting heap will render it quite harmless. All the organisms that cause human diseases are adapted to live around human body temperature. Higher temperatures kill them. Compost that stays at 50° C. (122° F.) for 24 hours will be safe to use to grow food. A temperature of 46° C. (115° F.) will kill pathogens within a week. 62° C. (143.6° F.) will kill pathogens in one hour.

In any embodiment of the bioreactor system 100, the electrical control assembly 201 comprises a temperature control system 225 comprising at least one of: a vented ducting arrangement 115, valving 230 and a pump 233 for forced air infusion; a closed ducting arrangement, valving and a pump for water cooling; a closed ducting arrangement 111, valving 231 and a pump 234 for refrigerant-type cooling; an automated turning systems to disrupt the organic waste matter 243; an infrared system (not shown); closed ducting arrangement (not shown), valving and pump for water heating (not shown); an electric coiled system for heating (not shown) and a gas burner system for heating (not shown).

In any embodiment of the bioreactor, the bioreactor electrical control assembly 201 is configured to control the temperature of the organic matter such that it will reach a thermophilic temperature greater than at least about 50° C. (122° F.) but less than about 76° C. (169° F.), for the minimum period of time necessary to substantially render any pathogens harmless to humans before further allowing the organic waste matter temperature to drop to an ambient temperature at a natural thermophilic rate.

In any embodiment of the bioreactor, the bioreactor electrical control assembly 201 is configured to control the temperature of the organic matter such that it will reach a thermophilic temperature of greater than at least about 55° C. (131° F.) but less than about 76° C. (169° F.).

In any embodiment of the bioreactor, the organic waste matter temperature is prevented from exceeding a maximum thermophilic temperature with the temperature control system.

As the temperature rises above about 40° C., the mesophilic microorganisms become less competitive and are replaced by others that are thermophilic, or heat-loving. At temperatures of 55° C. and above, many microorganisms that are human or plant pathogens are destroyed. Because temperatures over about 65° C. kill many forms of microbes and limit the rate of decomposition, compost managers use aeration and mixing to keep the temperature below this point.

During the thermophilic phase, high temperatures accelerate the breakdown of proteins, fats, and complex carbohydrates like cellulose and hemicellulose, the major structural molecules in plants. As the supply of these high-energy compounds becomes exhausted, the compost temperature gradually decreases and mesophilic microorganisms once again take over for the final phase of "curing" or maturation of the remaining organic matter.

In any embodiment of the bioreactor, the ambient temperature of the organic waste matter in the vermiculture chamber is controlled by the temperature control system.

In any embodiment of the bioreactor, an ambient temperature of the organic waste matter in the vermiculture chamber is controlled between about 10° C. (50° F.) and about 29° C. (84° F.).

By combining thermophilic composting with vermicomposting the inventors have found ways to generate a stable biofertilizer free of phytotoxicity and comprising no outright risk to human health in the form of organisms that cause human diseases.

In one preferred embodiment of the present invention, the inventors can assure their end products don't have any outright risks to humans because sensors 121 in the thermophilic chamber 110 measure the temperature, and registers if it meets the criteria for killing pathogens. Once the waste reaches those standards, the computer-implemented system 300 can then release the thermophilically composted organic waste 109 as "cooled" thermophilically composted organic waste 118 into the second (vermicomposting) chamber 120. If the waste does not meet the criteria for killing pathogens, then the computer-implemented system 300 prevents the thermophilic chamber from releasing into the vermicomposting chamber. This system prevents at-risk waste from ever becoming a product.

Additionally, vermicomposting alone naturally kills/inactivates human pathogens, given enough time. However, when combined with thermophilic composting, the combination further prevents producing a potentially harmful product in a much faster period of time. As for phytotoxicity, the system can ensure that the final product produced with this system is not phytotoxic because the curing phase in the vermicomposting chamber, which includes between 3-4 weeks at room temperature (between about 15°-27° C.) and the curing phase which lasts about 1-2 weeks at room temperature, help reduce the C:N ratio to a level that is accepted as an industry standard for healthy vermicompost. Overall, the time for a full cycle is approximately between 1.5 months to 2 months. The anticipated % target yield will be about 75%, but this will likely have a significant ± range based on the starting waste that is processed.

As noted previously, in any embodiment of the bioreactor system, the vermicomposting chamber 120 comprises a microporous bottom surface 125 through which the finished healthy vermicompost (humus) 130 will pass when knocked loose by the cutting bar 128.

In any embodiment of the bioreactor, the porous bottom surface 125 comprises at least one of: a screen; a wire mesh; a grid: straining surface and a sieve.

In any embodiment of the bioreactor, the porous bottom surface 125 has a plurality of sieve or mesh openings having a size of about 4.0 inches (101.6 mm) or smaller.

In any embodiment of the bioreactor, the porous bottom surface 125 has a plurality of sieve or mesh openings having a size of about 3.0 inches (76.2.0 mm) or smaller.

In any embodiment of the bioreactor, the porous bottom surface 125 has a plurality of sieve or mesh openings having a size of about 2.0 inches (50.8 mm) or smaller.

In any embodiment of the bioreactor, the porous bottom surface 125 has a plurality of sieve or mesh openings having a size of about 1.0 inch (25.4 mm) or smaller.

In any embodiment of the bioreactor, the porous bottom surface 125 has a plurality of sieve or mesh openings having a size of about 0.5 inch (12.7 mm) or smaller.

In any embodiment of the bioreactor, the porous bottom surface 125 has a plurality of sieve or mesh openings having a size of about 0.25 inch (6.35 mm) or smaller.

In any embodiment of the bioreactor, the porous bottom surface 125 has a plurality of sieve or mesh openings having a size of about 0.158 inch (4.0 mm) or greater.

In any embodiment, the bioreactor further comprises a removable receptacle for capturing the stable biofertilizer dropping through the porous bottom surface.

Provided herein is a method of converting organic waste matter into a stable biofertilizer utilizing thermophilic composting and vermicomposting comprising: a) providing a portable, climate-controlled, continuous flow-through, computer-operated vermiculture bioreactor 100 comprising: a gravity-fed, thermophilic decomposing chamber 110; and an interconnected vermicomposting chamber 120; wherein the thermophilic decomposing chamber comprises a gravity-feeding inferior base surface 105 positioned at a downward slope equal to or greater than about 30° relative to a side release door 106; b) providing an organic waste with biologic origins 108, primarily composing carbon and nitrogen;

c) depositing said organic waste in the gravity-fed, thermophilic decomposing chamber 110; d) controlling the temperature of said organic waste to heat to a thermophilic temperature between at least about 50° C. (122° F.)-55° C. (131° F.), but less than about 76° C. (169° F.) for a time sufficient to substantially render any pathogens harmless to humans; e) controlling the temperature of said heated organic waste matter to cool to an ambient temperature at a natural thermophilic rate; f) inoculating said organic waste matter with lignin-degrading fungi and bacteria; g) controlling a temperature, a relative humidity, a moisture and a pH of said organic waste; h) infusing adequate air, nutrients and water as needed into the organic waste matter to ensure aerobic composting; i) promoting thermophilic composting for a time sufficient to break down the lignin in the organic waste with thermophilic bacteria to an acceptable state; j) transferring the thermophilically composted organic waste to the interconnected vermicomposting chamber 120; k) controlling the temperature of the interconnected vermicomposting chamber between at least about 10° C. (50° F.) and about 29° C. (84° F.); l) providing adequate quantities of annelids 119 in the interconnected vermicomposting chamber to assure a predictable rate of vermicomposting; m) inoculating said thermophilically composted organic waste in the vermicomposting chamber with a plurality of microbial inoculum, hormones and nutrients; n) removing a portion of the vermicastings and granular biofertilizer generated by the vermicomposting in an automated fashion from the bottom of the vermicomposting chamber, at a scheduled rate coinciding with the predictable rate of vermicomposting; and o) repeating steps b)-o).

In any embodiment, the method further comprises, providing perforated aeration ducting arrangement 115, valving 230 and an air pump 233 to provide forced aeration to ensure aerobic composting.

In any embodiment, the method further comprises, providing a computer-implemented system comprising: a digital processing device 260 comprising: a breadboard circuit 265; at least one processor/microprocessor 2601; an operating system 2602 configured to perform executable instructions; a memory 2603 and at least one computer program 2604 including instructions executable by the digital processing device configured to interface with and control the bioreactor, bioreactor sub-components and the sensors 121, and communicate with remote monitoring facilities 280 with a receiver/transmitter device 2605. In some embodiments of the method, the system is further configured to take advantage of cloud computing 290 and storage utilizing the receiver/transmitter device 2605 and/or the remote monitoring facilities 280.

In any embodiment, the method further comprises, providing at least one of: a temperature sensor; a relative humidity sensor; a moisture sensor; a chemical sensor; an $O_2$ sensor; a $N_2$ sensor; a $CO_2$ sensor and a pH sensor; each sensor 121 configured to interface with the computer-implemented system.

In any embodiment, the method further comprises, providing a locking mechanism 107.

In some embodiments of the method, the locking mechanism is an auger-type locking mechanism 107 capable of opening and then closing the side release door 106 to assure closure against soft and/or friable debris that may obstruct the door after allowing the thermophilically composted organic waste matter 109 to pass between the decomposing chamber 110 and vermicomposting chamber 120.

In any embodiment, the method further comprises, providing at least one high-torque stepper motor 240, at least one motor controller 245 and at least one relay 248 to drive any one of a plurality of pumps 233,234 and valving 230, 231.

In some embodiments of the method, the high-torque stepper motor 240, motor controller 245 and relay 248 are interfaced with the auger-type locking mechanism 107 and the computer-implemented system 300.

In any embodiment, the bioreactor system further comprises at least one auger-type mechanism 243, as illustrated in FIG. 6C. This at least one auger-type mechanism 243 can be any form of known auger-type mechanism utilized as a conveyance means to move (typically granular and slurry) materials.

In any embodiment of the method, the bioreactor system further comprises a high-torque stepper motor 240, motor controller 245 and relay 248 to drive the at least one auger-type mechanism 243.

In any embodiment of the method, a movement of the organic waste matter through the bioreactor is accomplished via the at least one auger-type mechanism 243.

As further illustrated in FIGS. 6A and 6B, in some embodiments of the method, the high-torque stepper motor 240, motor controller 245 and relay 248 are interfaced with the auger-type mechanism 243 and the computer-implemented system 300.

In any embodiment of the method, the plurality of microbial inoculum, nutrients and hormones injected into the vermicomposting chamber comprise at least one of: the beneficial microbes comprising at least one of: rhizobia; and blue-green cyanobacteria; and the beneficial fungi comprise at least one of: arbuscular mycorrhiza fungi (AMF); *Trametes versicolor*; *Phanerochaete chrysosporium*; *Basidiomycetes*; *Ascomycetes* and *Deuteromycetes*; and the nutrients comprising at least one of: calcium carbonate; magnesium; crushed limestone; carbon; urea; potassium; phosphorous and nitrogen; and the hormones comprising at least one of: Indole-3-acetic acid; gibberellic acid; auxins; cytokinins; gibberellins; abscisic acid and ethylene, or any combination of the optional plurality of microbial inoculum, nutrients and hormones recited herein.

In any embodiment of the method, the computer-implemented system of the bioreactor system further comprises the ability to take advantage of cloud computing and storage of data utilizing sensor information.

Provided herein is a portable, climate-controlled, continuous flow-through, computer-operated vermiculture bioreactor 100 for converting raw organic waste matter 108 into a stable biofertilizer 130 utilizing thermophilic composting and vermicomposting comprising: a decomposing chamber 110 having a first side wall 103 and a second side wall 104 with a release door 106, a first end wall 101, a second end wall 102 and a base 105 having a downward slope between the first side wall and a bottom edge of the release door 106(a) and further comprising aeration ducting 115 to provide oxygen to the organic waste matter; a vermicomposting chamber 120 mounted below the side release door of the decomposing chamber having four side walls and a porous bottom surface 125; a plurality of sensors 121 for environmental monitoring of the bioreactor and the organic waste matter; a computer-implemented system 300 comprising: a digital processing device or micro-controller 260 comprising: a breadboard circuit 265; at least one processor or microprocessor 2601, an operating system 2602 configured to perform executable instructions, a memory 2603, and a computer program 2604 including instructions executable by the digital processing device configured to interface with and control the bioreactor, bioreactor sub-components and the sensors 121, and communicate with remote monitoring facilities and/or take advantage of cloud computing and storage with a receiver/transmitter device 2605; wherein the decomposing chamber is configured for thermophilic composting to substantially eliminating pathogens from the raw organic waste matter; begin degrading the lignin with controlled thermophilic heating and cooling, making it palatable for annelids (worms) 119 and sowbugs in the vermicomposting chamber 120, wherein the vermicomposting chamber is configured to receive the substantially pathogen-free decomposed organic waste matter 109 from the decomposing chamber and house a plurality of annelids selected to consume the substantially pathogen-free decomposed organic waste matter, converting it to a stable biofertilizer 130, wherein the plurality of sensors 121 interface and communicate with the computer-implemented system to provide real-time environmental data about the organic waste matter throughout the composting process, and wherein the computer-implemented system collects and reports environmental data and controls automated operation of a plurality of mechanical and electrical functions associated with the bioreactor or sub-components thereof. In any embodiment of the bioreactor system 100, the computer-implemented system 300 further comprises the ability to take advantage of remote monitoring facilities 280, cloud computing and storage of data 290, communicating with remote monitoring facilities 280, and/or cloud computing and storage 290 through any common form of communication, with a receiver/transmitter device 2605 which includes, by way of non-limiting examples, direct (hard wired) communication means, cellular, Wifi, an Intranet, the Internet, Bluetooth® or other wireless technology.

In any embodiment, the aeration ducting 115 comprises perforated ducting 117 connected to an air pump 233 and valving 230 configured to force air through the decomposing chamber 110 for aeration.

In any embodiment, the decomposing chamber 110 further comprises a temperature control system comprising at least one of: a vented ducting arrangement 115,117, valving 230 and a pump 233 for forced air infusion, a closed ducting arrangement (not shown), valving 231 and a pump 234 for water cooling; a closed ducting arrangement (not shown), valving 231 and a pump 234 for refrigerant-type cooling; a mechanical turning system (not shown) to disrupt the organic waste matter; an infrared heating system (not shown); a closed ducting arrangement (not shown), valving 231 and a pump 234 for water heating; an electric coiled system for heating (not shown); and a gas burner system for heating (not shown).

In any embodiment, the bioreactor further comprises at least one high-torque stepper motor 240, at least one motor controller 245 and at least one relay 248 to drive any one of a plurality of pumps 233, 234 and valving 230, 231.

In any embodiment, the bioreactor further comprises injectors 112 in the decomposing chamber 110 connected to a pump 234 and valving 231 configured to add water to the raw decomposing organic waste matter 108 to ensure that adequate moisture is maintained throughout the thermophilic decomposing process.

In any embodiment of the decomposing chamber 110, the slope of the base 105 is about 30°. In some embodiment, the downward slope of the base 105 is equal to or greater than about 30°. In some embodiments, the downward slope of the base 105 is equal to or less than about 30°.

However, depending on the lubricity of the sloped surface, the slope of the base can have a range anywhere between about 10.0° and about 60.0°. In some embodiments, the slope of the base is: 7.5°, 10.0°, 12.5°, 15.0°, 17.5°, 20.0°, 22.5° 25.0°, 27.5°, 30.0°, 32.5°, 35.0°, 37.5°, 40.0°, 42.5°, 45.0°, 47.5°, 50.0°, 52.5°, 55.0°, 57.5° or 60.0°.

In any embodiment, the plurality of sensors 121 comprise at least one of: a temperature sensor; a relative humidity sensor, a moisture sensor, a chemical sensor, an $O_2$ sensor, a $N_2$ sensor, a $CO_2$ sensor and a pH sensor.

In any embodiment, the bioreactor further comprises a plurality of inoculating pumps 234 and valving 231 configured to inoculate both the decomposing chamber 110 and the vermicomposting chamber with a plurality of microbial inoculum, hormones and nutrients.

In any embodiment, the microbial inoculua of the decomposing chamber comprise lignin-degrading fungi and bacteria.

In any embodiment, the fungi comprise at least one of: arbuscular mycorrhiza fungi (AMF); *Trametes versicolor; Phanerochaete chrysosporium; Basidiomycetes; Ascomycetes*; and *Deuteromycetes*.

In any embodiment, the bacteria comprise at least one of: *Pseudomonas; Flavobacterium*; filimentous bacteria or Actinomycetes and *Thermus* bacteria.

In any embodiment, the microbial inoculua of the vermicomposting chamber comprise microbes beneficial to plant use and can perform at least one of the following functions: promote nutrient acquisition; promote plant growth; promote plant health; promote disease prevention; promote drought resistance; promote insect resistance and kill insects.

In any embodiment, the beneficial microbes comprise at least one of: rhizobia; blue-green cyanobacteria and arbuscular mycorrhiza fungi (AMF).

In any embodiment, the nutrients comprise at least one of: calcium carbonate; magnesium; carbon; urea; potassium; phosphorous and nitrogen. For the purposes of this application, crushed limestone is particularly useful for improving pH and increasing calcium or magnesium in the end-product. As was also noted previously, $H_2SO_4$ (which can decrease pH) is optionally used as an additive to the fertilizer, as well as blood meal, feather meal, and bone meal which can be used to further improve biofertilizer quality.

In any embodiment, the hormones of the vermicomposting chamber comprise at least one of: Indole-3-acetic acid; gibberellic acid; auxins; cytokinins; gibberellins; abscisic acid and ethylene.

In any embodiment, the vermicomposting chamber 120 further comprises a cutting bar 128 configured to periodically traverse the length of the chamber, near the bottom, to encourage the processed biofertilizer to fall through the porous bottom surface 125.

In any embodiment, a bioreactor power system further comprises at least one solar panel 210 and at least one DC battery 220.

In any embodiment, the bioreactor further comprises a power bank 270 to store energy and perform step-down voltage requirements.

In any embodiment, the power system comprises two or more solar panels 210.

In any embodiment, the DC battery 220 comprises a deep-cycle battery.

In any embodiment, the plurality of annelids 119 comprise at least one annelid from a list of species comprising: *Eisenia fetida* and *Eisenia hortensis*.

In any embodiment, the stable biofertilizer 130 generated therein comprises a carbon to nitrogen ratio of less than 25 parts carbon to 1 part nitrogen.

In any embodiment, the stable biofertilizer 130 generated therein comprises no outright risk of phytotoxicity.

In any embodiment, the stable biofertilizer 130 generated therein comprises no outright risk to human health in the form of organisms that cause human diseases.

In any embodiment, the bioreactor further comprises a locking mechanism 107 capable of closing the release door 106 and configured to assure closure against soft and/or friable debris that may obstruct the door after allowing the thermophilically treated organic waste matter 109 to pass between the decomposing chamber 110 and vermicomposting chamber 120.

In any embodiment, the bioreactor further comprises at least one auger-type mechanism 243, 107.

In any embodiment, the bioreactor further comprises a high-torque stepper motor 240, motor controller 245 and relay 248 to drive the at least one auger-type mechanism 243.

In any embodiment, a movement of the organic waste matter through the bioreactor is accomplished via the at least one auger-type mechanism 243. This at least one auger-type mechanism 243 can be any form of known auger-type mechanism utilized as a conveyance means to move (typically granular and slurry) materials.

In some embodiments, the high-torque stepper motor 240, motor controller 245 and relay 248 are interfaced with the auger-type mechanism 243 and the computer-implemented system 300.

In any embodiment, the locking mechanism 107 is an auger-type locking mechanism.

In any embodiment, the bioreactor further comprises a high-torque stepper motor 240, motor controller 245 and relay 248 to drive the auger-type locking mechanism 107.

In any embodiment, a movement of the organic waste matter through the bioreactor is accomplished via gravity. In any embodiment, a movement of the organic waste matter through the bioreactor is accomplished via a combination of mechanical forces and gravity. In any embodiment, a movement of the organic waste matter through the bioreactor is accomplished mechanical forces such as cutting bars 128, pushing bars and/or auger mechanisms 243.

In any embodiment of the bioreactor, the perforated ducting 115, 117 comprises at least one of: PVC piping; stainless steel piping; rubber tubing and plastic tubing.

In any embodiment of the bioreactor, the porous bottom surface 125 comprises at least one of: a screen; a wire mesh; a grid: straining surface and a sieve.

In any embodiment of the bioreactor, the porous bottom surface 125 has a plurality of sieve or mesh openings having a size of about 1.0 inch (25.4 mm).

In any embodiment of the bioreactor, the porous bottom surface 125 has a plurality of sieve or mesh openings having a size between about 4.0 inches (101.6 mm) or smaller and about 0.158 inch (4.0 mm) or greater.

In any embodiment, the bioreactor further comprises a removable receptacle 145 for capturing the stable biofertilizer dropping through the porous bottom surface 125.

In any embodiment, the bioreactor system further comprises a temperature control system.

In any embodiment of the bioreactor, the bioreactor temperature control system is configured to control the temperature of the organic matter such that it will reach a thermophilic temperature greater than at least about 50° C. (122° F.) but less than about 76° C. (169° F.), for a minimum period of time necessary to substantially render any pathogens harmless to humans before further allowing the organic waste matter temperature to drop to an ambient temperature at a natural thermophilic rate.

In any embodiment of the bioreactor, the bioreactor temperature control system is configured to control the temperature of the organic matter such that it will reach a thermophilic temperature of greater than at least about 55° C. (131° F.) but less than about 76° C. (169° F.).

In any embodiment of the bioreactor, the organic waste matter temperature is prevented from exceeding a maximum thermophilic temperature with the temperature control system.

In any embodiment of the bioreactor, an ambient temperature of the organic waste matter in the vermiculture chamber is controlled between about 10° C. (50° F.) and about 29° C. (84° F.) by the bioreactor temperature control system.

In any embodiment of the bioreactor, the ambient temperature of the organic waste matter in the vermiculture chamber is controlled by the temperature control system.

In any embodiment of the bioreactor, the temperature control system comprises at least one of: a vented ducting arrangement 115,117, valving 230 and a pump 233 for forced air infusion, a closed ducting arrangement (not shown), valving 231 and a pump 234 for water cooling; a closed ducting arrangement (not shown), valving 231 and a pump 234 for refrigerant-type cooling; a mechanical turning system (not shown) to disrupt the organic waste matter; an infrared heating system (not shown); a closed ducting arrangement (not shown), valving 231 and a pump 234 for water heating; an electric coiled system for heating (not shown); and a gas burner system for heating (not shown).

Figure 5:
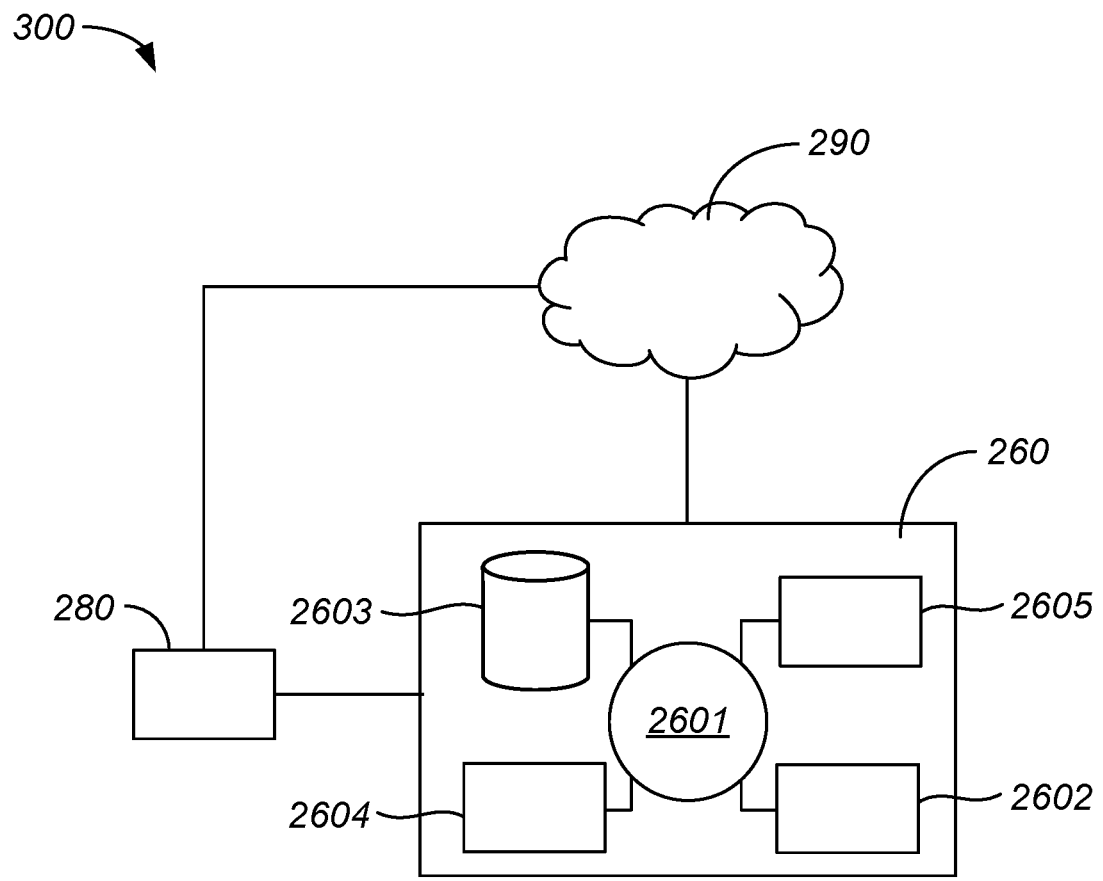
FIG. 5 is a non-limiting pictorial representation of the computer-implemented bioreactor system.

In any embodiment of the bioreactor system, the computer-implemented system 300 further comprises the ability to take advantage of cloud computing and storage of data 290 as illustrated in FIG. 5.

Figure 7:
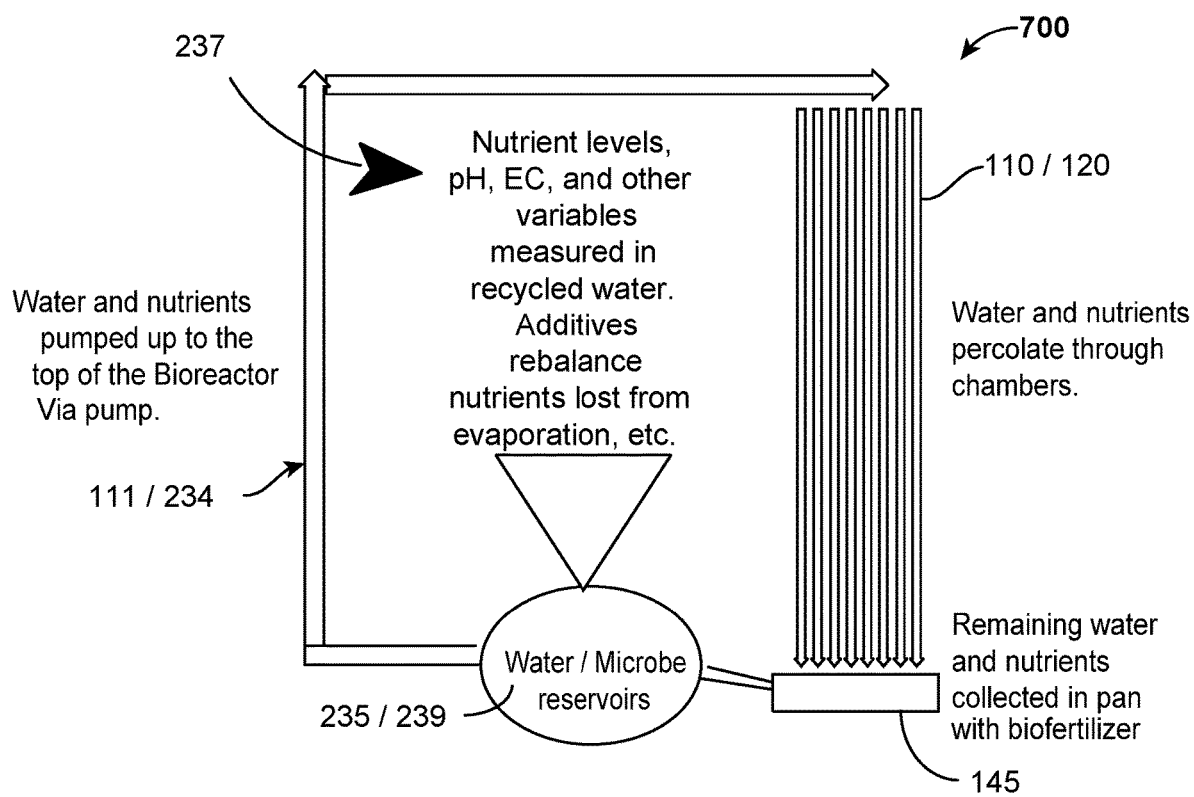
FIG. 7 is a non-limiting illustration of a reservoir recirculating system.

In some embodiments, the water reservoir tank and microbe reservoirs 235, 239, such as the non-limiting reservoir recirculating system 700, illustrated in FIG. 7, are configured to direct an aqueous nutrient solution from the water reservoir tank and microbe reservoirs 235, 239, pumped up to the tops of the chambers via a pump and piping system 111, 234, and distributed through the upper portions of the chambers 110, 120, in a controlled flow, allowing the water, microbes and nutrients to percolate through the chambers. Optionally, additional distribution points at lower points in the chambers may also be utilized for secondary distribution of water with balanced nutrient levels to account for losses, evaporation and absorption in the chamber(s) above as measured in the water runoff collection tank 237. Once the water and nutrients complete the vertical traverse, the remaining water and nutrients that leave the lowest chamber 120, are collected in a pan 145, and recycled to the water reservoir 235. In some embodiments where human waste is included within the vertical traverse and processed through the thermophilic composting cycle, the water would not be recycled in order to avoid the remote possibility of redistributing any human pathogens back into the compost. However, in yet other embodiments, a special water filtration system (not shown) would be utilized that would allow for recirculating the water for all wastes.

In some embodiments, a master control system 800 further comprises at least one of: a software module 801 comprising stored algorithms 811, configured to regulate a temperature; a software module configured to regulate a humidity; a software module configured to regulate a gaseous or an aqueous $CO_2$ and/or $O_2$ content; a software module configured to regulate an airflow; a software module configured to regulate a flow of water and nutrients; a software module configured to regulate an aqueous nutrient/microbe concentration of an aqueous nutrient/microbe solution; a software module configured to regulate an aqueous pH; a software module configured to regulate a water oxidation reduction potential (ORP); a software module configured to regulate an aqueous electrical conductivity (EC); in response to the instructions. In some embodiments, the processing device further comprises a receiver for receiving transmitted data. In some embodiments, the processing device further comprises a transmitter for transmitting data. In some embodiments, the receiver and transmitter are configured for wired or wireless receipt or transmission of data. In some embodiments, the master control system is further configured to automatically monitor and adjust one or more of the environmental conditions in the environmentally-controlled bioreactor in response to the instructions. In some embodiments, the bioreactor characteristic is humidity. In some embodiments, the bioreactor characteristic is temperature. In some embodiments, the control system further comprises a plurality of the sensors placed in a plurality of sensor units to provide environmental condition data corresponding with a sufficient quantity of the bioreactor modules that the environmental condition for any other bioreactor module in the system is predictable based on the provided data at a 95% confidence level. In some embodiments, the control system further comprises at least one additional sensor that measures another environmental condition in the environmentally-controlled bioreactor chamber over time to generate additional environmental condition data, wherein the software module is configured for receiving the additional environmental condition data from the environmental sensor and the measuring device; further wherein the software module is configured to apply an algorithm to the environmental condition data, the additional environmental data, and the bioreactor data to generate improved composting conditions and store the improved environmental composting conditions in the memory, and wherein the software module is configured for generating and transmitting the instructions for adjustment of the environmental composting conditions in or around the bioreactor sensor modules to a sub-system in the environmentally-controlled bioreactor chamber to implement the improved environmental composting conditions.

Provided herein is a computer-implemented control system for a bioreactor vermiculture composting system, the system comprising: at least first and second composting chambers in an environmentally-controlled vermiculture bioreactor; a device that measures a composting characteristic of a first composting module of the environmentally-controlled vermiculture composting system to generate composting data; a sensor for placement in a sensor unit mounted in or on the second composting chamber, the second composting chamber configured to permit vertical flow of an aqueous nutrient/microbe solution through itself, thereby forming a vertically stacked or tiered vermiculture composting system, wherein the sensor measures an environmental composting condition in the environmentally-controlled vermiculture composting chamber over time to generate environmental condition data, further wherein the sensor unit measures data corresponding to a first composting condition at a second vermicomposting module over time, the first composting condition selected from the group consisting of humidity, ambient carbon dioxide concentration, ambient oxygen concentration, airflow speed, air pressure and temperature of the controlled environment, further wherein the sensor unit is not permeable to water, and is permeable to gases, permitting passage of gases therethrough and permits insulation of carbon dioxide or other gas sensors for use in wet conditions of the environmentally-controlled composting chamber; and a processing device comprising at least one processor, a memory, an operating system configured to perform executable instructions, and a computer program including instructions executable by the processing device to create an application comprising: a software module configured to receive the environmental condition data and the composting/vermicomposting data from the environmental sensor and the measuring device; a software module configured to apply an algorithm to the environmental condition data and the chamber data to generate an improved environmental composting condition and store the improved environmental composting condition in the memory; and a software module configured to generate and transmit instructions for adjustment of the environmental composting condition in or around the chamber(s) to a sub-system of the environmentally-controlled chamber(s) to implement the improved environmental composting condition. In some embodiments, the vermiculture composting system is configured to supply the aqueous nutrient/microbe solution, through a water and nutrient supply system, to media in the vermiculture chamber(s), and wherein the environmental composting condition comprises: a temperature of the nutrient solution, an air temperature in the controlled environment, a humidity in the controlled environment, an ambient oxygen gas concentration in the controlled environment, an ambient carbon dioxide concentration in the controlled environment, an airflow in the controlled environment, and/or a nutrient solution flow rate. In some embodiments, the control system further comprises at least one of: a software module configured to regulate a temperature; a software module configured to regulate a humidity; a software module configured to regulate a gaseous or an aqueous $CO_2$ and/or $O_2$ content; a software module configured to regulate an airflow; a software module configured to regulate an air pressure; a software module configured to regulate a flow of water and nutrients; a software module configured to regulate an aqueous nutrient/microbe concentration of an aqueous nutrient solution; a software module configured to regulate an aqueous pH; a software module configured to regulate a water oxidation reduction potential (ORP); a software module configured to regulate an aqueous electrical conductivity (EC); or a software module configured to regulate a movement of the cutting bar within the second chamber; in response to the instructions. In some embodiments, the sensor for placement in the sensor unit mounted in or on the second chamber further measures data corresponding to a second environmental vermicomposting condition inside the second chamber over time. In some embodiments, the second environmental composting condition comprises a characteristic of the aqueous crop nutrient solution. In some embodiments, the environmental growing condition comprises: an air temperature inside the second chamber; a humidity inside the second chamber; an airflow inside the second chamber; a temperature of the aqueous nutrient/microbe solution; a pH of the aqueous nutrient/microbe solution; an electrical conductivity of the nutrient/microbe solution; a flow rate of the aqueous nutrient/microbe solution; an aqueous nutrient/microbe concentration of the aqueous nutrient/microbe solution; a pH of the aqueous nutrient/microbe solution; a dissolved $O_2$ concentration of the aqueous nutrient/microbe solution; a dissolved $CO_2$ concentration of the aqueous nutrient/microbe solution; a water oxidation reduction potential (ORP) of the aqueous nutrient/microbe solution; an electrical conductivity (EC) of the aqueous nutrient/microbe solution; a microbe composition of the aqueous nutrient/microbe solution or a nutrient composition of the aqueous nutrient/microbe solution. In some embodiments, the processing device further comprises a receiver for receiving transmitted data. In some embodiments, the processing device further comprises a transmitter for transmitting data. In some embodiments, the receiver and transmitter are configured for wired or wireless receipt or transmission of data. In some embodiments, the control system is further configured to automatically monitor and adjust one or more of the environmental composting conditions in the environmentally-controlled composting/vermicomposting chambers in response to the instructions.

Figure 8:
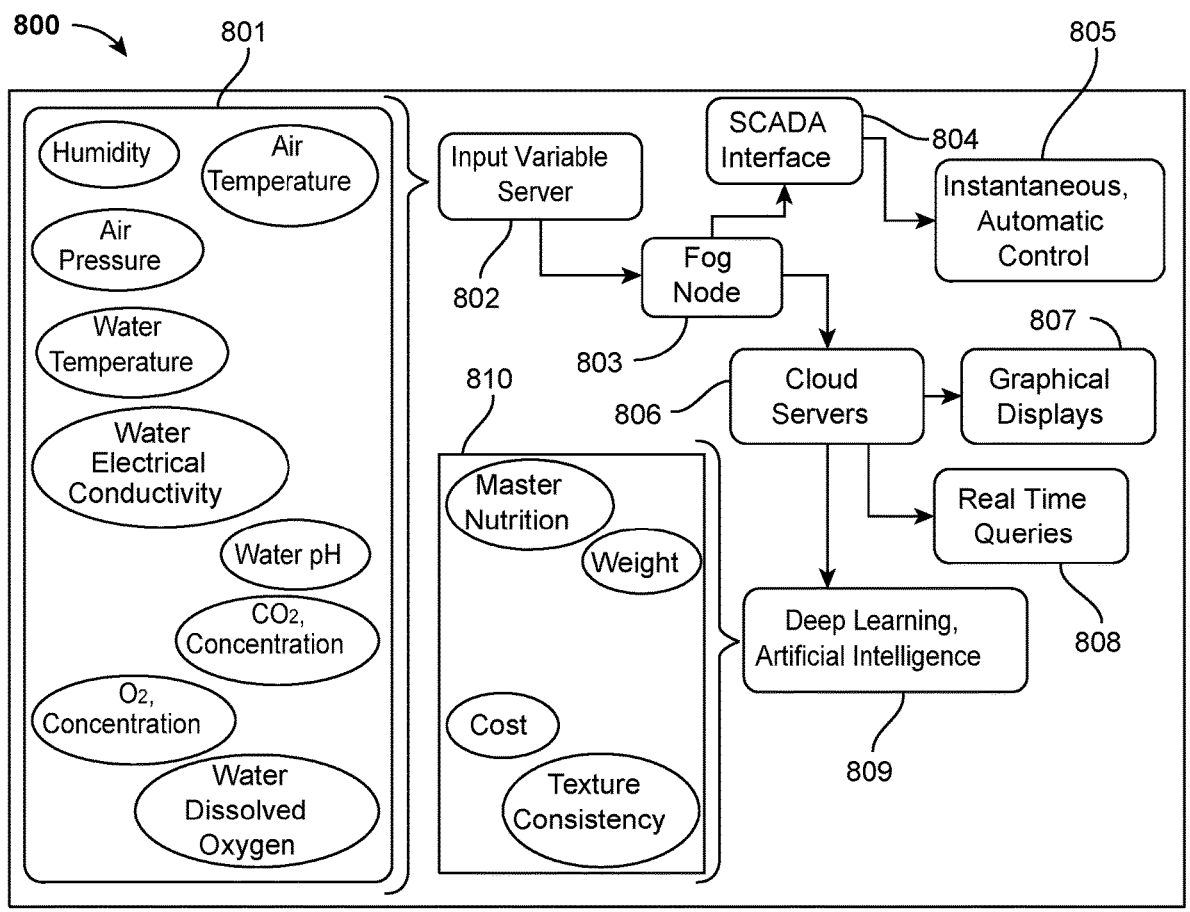
FIG. 8 is a non-limiting illustration of a computer control system.

In some embodiments, as illustrated in FIG. 8, the computer control system or master control system 800, comprises an artificial intelligence system comprising: an input variable server 802, a Fog Node 803, a SCADA interface 804 to provide instantaneous automatic control 805, Cloud Servers 806, Graphical Displays 807, the ability to accommodate and provide Real Time Queries 808 and software systems providing Deep Learning, Artificial Intelligence programming 809. When properly programmed and combined, the master control system 800 monitors composting conditions of the enclosed composting/vermicomposting Bioreactor Assembly system, 100, the first and second composting/vermicomposting chambers 110, 120 and individual sub-systems within the enclosed composting/vermicomposting Bioreactor Assembly system, analyzing the input data from the monitored composting conditions provided by the sensors 121 and composting characteristic measuring devices 821, sent to the sensor arrays 121 and subsequently transmitted to the master control system 800 for processing. Once this data is collected and analyzed, the master control system 800 is configured, through Deep Learning, Artificial Intelligence programming 809, to adjust composting conditions by sending out new instructions to the various environmental control systems and software modules 801 comprising stored algorithms 811 and nutrient/microbe control systems 235,239 in order to improve and continually optimize the output characteristics of the Bioreactor Assembly system, 100.

Figure 9:
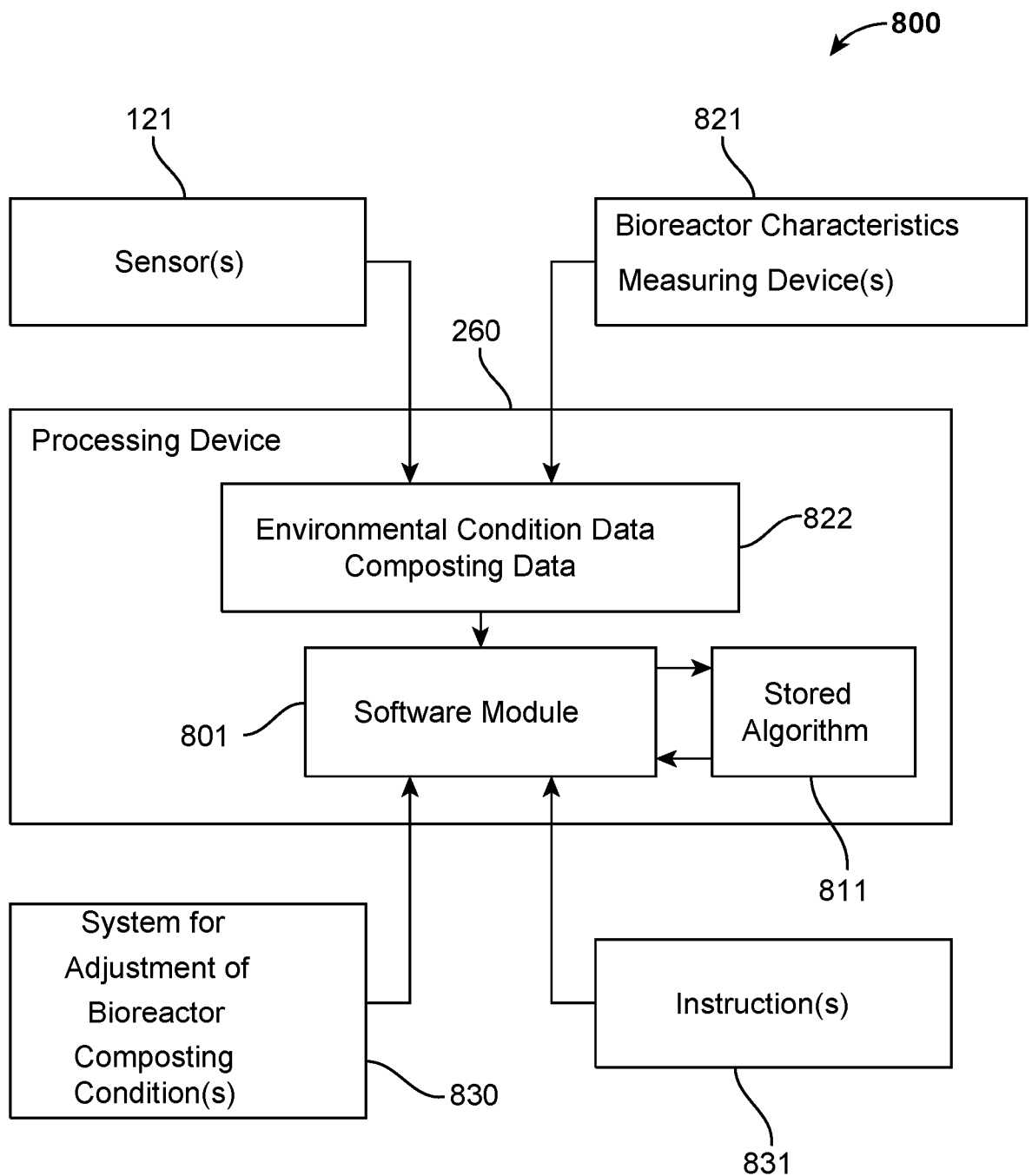
FIG. 9 is another non-limiting illustration of a computer control system.
Figure 10:
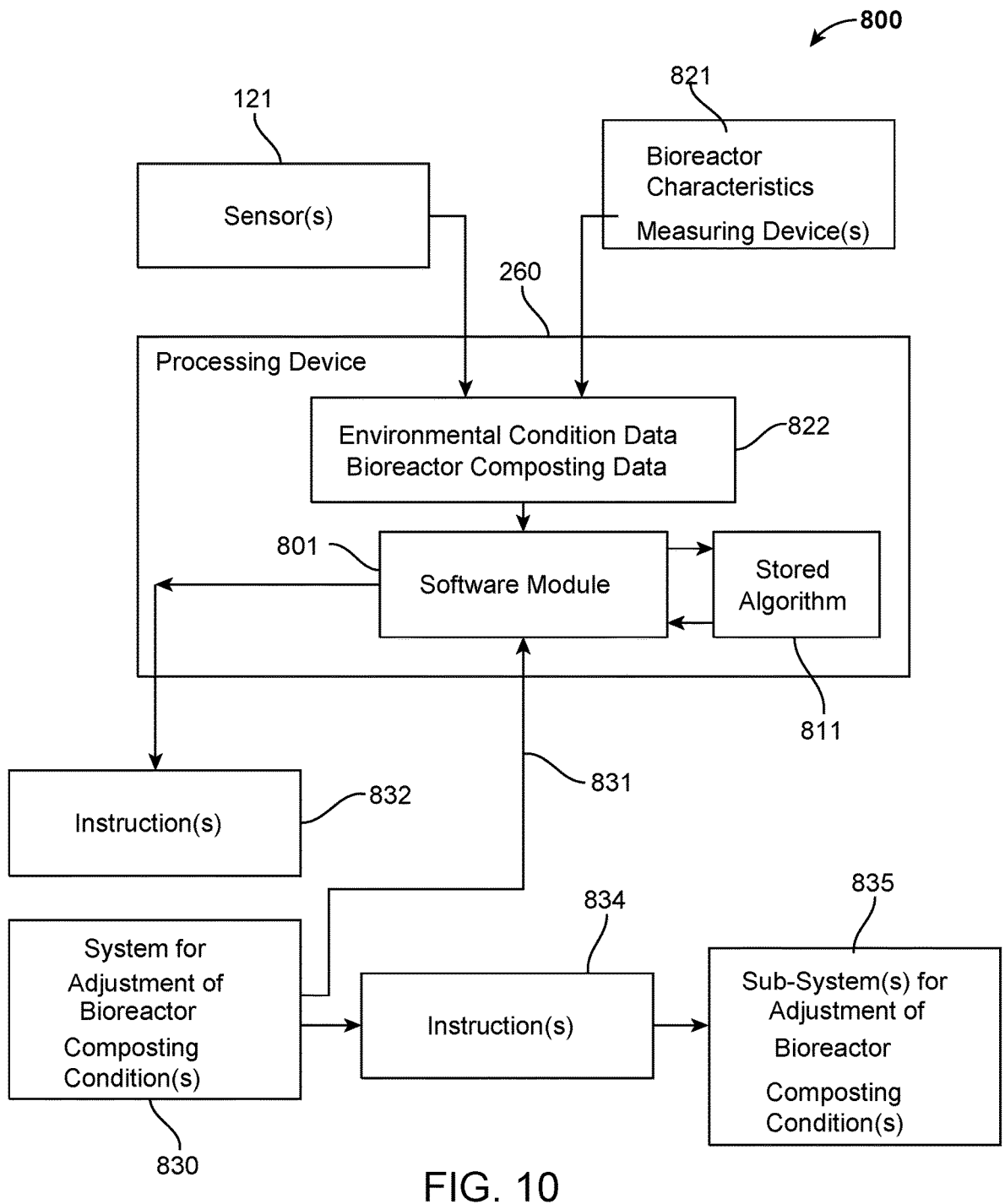
FIG. 10 is another non-limiting illustration of a computer control system.

As illustrated in FIGS. 9 and 10, when properly programed and combined the master control system 800 monitors the Output Characteristics 810 of the Bioreactor Assembly System 100, 201, the Decomposing Chamber 110 and Vermiculture Chamber 120, analyzing the input data from the Output Characteristics Software Module 810 provided by the sensors 121 and bioreactor characteristic measuring devices 821, sent to the sensor arrays (not shown), collected and collated into the environmental condition data and composting databases 822 and subsequently transmitted to the master control system 800 for processing by the processing device 260. Once this data is collected and analyzed, the master control system 800 is configured, through Deep Learning, Artificial Intelligence programming 809, to adjust growth conditions by sending out new instructions 831, 832, 834 to the various bioreactor environmental control systems 830, 835 and nutrient reservoir control systems 700 in order to improve and continually optimize the output characteristics 810 of the biofertilizer 130.

In some embodiments of the Bioreactor Assembly System 100, 201, the output characteristics 810 of the biofertilizer comprise nutrition levels, weight, growth (manufacturing/production) costs, color or appearance, and/or texture.

In some embodiments of the Bioreactor Assembly system, 100 the output characteristics 810 of the chamber(s) comprise nutrition/microbe levels, weight, (manufacturing/production) costs, or appearance, and/or texture.

The sensor(s) may be configured for placement in a sensor unit 110, which itself is configurable for placement in a chamber 110, 120 or a sensor module (not shown), which may or may not include a compost material therein. This second "dummy" composting module (not shown), to (and/or inside of) which the sensor is mounted, may be configured to stackably support or monitor conditions outside of the Bioreactor Assembly system, 100.

In some examples, a plurality of sensors are distributed about the environmentally-controlled Bioreactor Assembly system 100, to provide environmental data 822 corresponding with their individual positions. In some examples, sensors 121 are distributed about one or more chambers, each corresponding with a position of a deposit of compost materials within the chamber. In preferred examples, a sufficient number of sensors is used such that environmental data (corresponding with one or more environmental condition(s) generated by this plurality of sensors such that the environmental condition(s) at any position within the chamber(s) (or within the system) may be predicted with 95% statistical confidence.

While preferred embodiments of the present invention have been shown and described herein, it will be obvious to those skilled in the art that such embodiments are provided by way of example only. Numerous variations, changes, and substitutions will now occur to those skilled in the art without departing from the invention, in accordance with the claims. It should be understood that various alternatives to the embodiments of the invention described herein may be employed in practicing the invention.

What is claimed is:

1. A gravity fed vermiculture bioreactor system for converting raw organic waste matter into a stable biofertilizer utilizing thermophilic composting and vermicomposting, the bioreactor comprising:
    a decomposing chamber for containing the organic waste matter during thermophilic composting and lignin degradation, the decomposing chamber having a sloped base and a door configured to direct thermophilically composted organic waste matter to a removable vermicomposting chamber below the decomposing chamber when the door is in an opened position;
    a plurality of sensors for monitoring an environmental condition of the organic waste matter in the decomposition chamber and the vermicomposting chamber; and
    a temperature control system comprising a closed ducting arrangement, a valve, and a pump for refrigerant-type cooling of at least one of the decomposing chamber and the vermicomposting chamber based on the environmental condition, wherein the temperature control system transmits data about the environmental condition remotely for data storage;
    wherein the vermicomposting chamber is configured to receive the thermophilically composted organic waste matter from the decomposing chamber and is further configured to contain the thermophilically composted organic waste matter during vermicomposting thereof.

2. The bioreactor system of claim 1, further comprising a forced-air system coupled to the decomposing chamber for directing air into the decomposing chamber and maintaining the contained organic waste matter within a thermophilic temperature range.

3. The bioreactor system of claim 2, further comprising:
    a computer-implemented system comprising:
        a digital processing device comprising:
            at least one processor;
            an operating system configured to perform executable instructions;
            a memory; and
        a computer program including instructions executable by the digital processing device configured to interface with and control the bioreactor, bioreactor sub-components and the sensors, and communicate with remote monitoring facilities or cloud computing and storage.

4. The bioreactor system of claim 3, wherein the slope base is configured to promote gravity transfer of the thermophilically composted organic waste matter from the decomposing chamber to the vermicomposting chamber.

5. The bioreactor system of claim 1, further comprising a locking mechanism capable of opening and then closing the door.

6. The bioreactor system of claim 1, wherein the vermicomposting chamber is configured to hold a plurality of annelids for consuming the thermophilically composted organic waste matter received from the decomposing chamber.

7. The bioreactor system of claim 6, wherein the vermicomposting chamber comprises a porous base.

8. The bioreactor system of claim 7, wherein the vermicomposting chamber further comprises a cutting bar configured to periodically traverse the length of the chamber, near the bottom, to encourage the processed biofertilizer to fall through the porous bottom surface.

9. The bioreactor system of claim 1, wherein the bioreactor is portable.

10. The bioreactor system of claim 3, further comprising injectors in the decomposing chamber connected to a second pump and valving configured to add water to the decomposing organic waste matter to maintain a moisture throughout the composting process.

11. The bioreactor system of any one of claim 10, further comprising a plurality of inoculating pumps and valving configured to inoculate both the decomposing chamber and the vermicomposting chamber with a plurality of microbial inoculum, hormones and nutrients.

12. The bioreactor system of claim 11, wherein the plurality of microbial inoculumm of the decomposing chamber comprise lignin-degrading fungi and bacteria.

13. The bioreactor system of claim 1, wherein the plurality of sensors comprise at least one of:
    a temperature sensor;
    a relative humidity sensor;
    a moisture sensor;
    a chemical sensor;
    an O2 sensor;
    a N2 sensor;
    a CO2 sensor; and
    a pH sensor;
each configured to interface with a computer-implemented system.

14. The bioreactor system of claim 1, wherein the decomposing chamber is configured to reach a thermophilic temperature greater than at least about 50° C. (122° F.) but less than about 76° C. (169° F.), for a minimum period of time necessary to substantially render any pathogens harmless to humans before further allowing the organic waste matter temperature to drop to an ambient temperature at a natural thermophilic rate.

15. The bioreactor system of claim 1, wherein an ambient temperature of the organic waste matter in the vermicomposting chamber is between about 10° C. (50° F.) and about 29° C. (84° F.).

16. The bioreactor system of claim 1, wherein the organic waste matter temperature is prevented from exceeding a maximum thermophilic temperature with the temperature control system.

17. The bioreactor system of claim 1, wherein the temperature control system further comprises at least one of:
   a vented ducting arrangement for forced air infusion;
   a closed ducting arrangement for water cooling;
   an automated turning system to disrupt the organic waste matter;
   an infrared system;
   a closed ducting arrangement for water heating;
   an electric coiled system for heating; and
   a gas burner system for heating.

18. The bioreactor system of claim 1, further comprising a master control system comprising:
   an artificial intelligence system comprising:
      an input variable server;
      a Fog Node;
      a SCADA interface to provide instantaneous automatic control;
      Cloud Servers;
      Graphical Displays;
      an ability to accommodate and provide Real Time Queries; or
      software systems providing Deep Learning, Artificial Intelligence programming.

\* \* \* \* \*